US012734274B2

(12) United States Patent
Badylak et al.

(10) Patent No.: US 12,734,274 B2
(45) Date of Patent: Sep. 15, 2026

(54) METHODS FOR PREPARATION OF A TERMINALLY STERILIZED HYDROGEL OR COLLOIDAL SUSPENSION DERIVED FROM EXTRACELLULAR MATRIX, AND USES THEREOF

(71) Applicant: University of Pittsburgh—Of the Commonwealth System of Higher Education, Pittsburgh, PA (US)

(72) Inventors: Stephen Francis Badylak, West Lafayette, IN (US); George S. Hussey, Cranberry Township, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 318 days.

(21) Appl. No.: 18/044,969

(22) PCT Filed: Apr. 30, 2021

(86) PCT No.: PCT/US2021/030134
§ 371 (c)(1),
(2) Date: Mar. 10, 2023

(87) PCT Pub. No.: WO2022/055559
PCT Pub. Date: Mar. 17, 2022

(65) Prior Publication Data

US 2023/0364301 A1 Nov. 16, 2023

Related U.S. Application Data

(60) Provisional application No. 63/077,084, filed on Sep. 11, 2020.

(51) Int. Cl.
*A61L 27/52* (2006.01)
*A61L 27/36* (2006.01)
*A61L 27/54* (2006.01)

(52) U.S. Cl.
CPC .......... *A61L 27/3633* (2013.01); *A61L 27/52* (2013.01); *A61L 27/54* (2013.01); *A61L 2400/06* (2013.01); *A61L 2430/34* (2013.01)

(58) Field of Classification Search
None
See application file for complete search history.

(56) References Cited

U.S. PATENT DOCUMENTS 4,902,508 A 2/1990 Badylak et al.
4,956,178 A 9/1990 Badylak et al.
(Continued)

FOREIGN PATENT DOCUMENTS

AU 2017235321 A1 9/2017
CN 102176900 A 9/2011
(Continued)

OTHER PUBLICATIONS

Hussey et al., "Ultrasonic cavitation to prepare ECM hydrogels," *ACTA Biomaterialia* 108:77-86, E-pub Apr. 5, 2020.
(Continued)

*Primary Examiner* — Ernst V Arnold
(74) *Attorney, Agent, or Firm* — Klarquist Sparkman, LLP

(57) ABSTRACT

A method is disclosed for treating a fistula in a subject, such as, but not limited to, an anal fistula. In some embodiments, the method includes administering locally to the fistula in the subject an effective amount of a composition comprising a mammalian acoustic extracellular matrix (ECM) hydrogel, and optionally trehalose. Compositions of use in these methods are also disclosed.

21 Claims, 9 Drawing Sheets

(56) References Cited

U.S. PATENT DOCUMENTS

| | | | |
|---|---|---|---|
| 5,281,422 A | 1/1994 | Badylak et al. | |
| 5,352,463 A | 10/1994 | Badylak et al. | |
| 5,372,821 A | 12/1994 | Badylak et al. | |
| 5,554,389 A | 9/1996 | Badylak et al. | |
| 5,573,784 A | 11/1996 | Badylak et al. | |
| 5,645,860 A | 7/1997 | Knapp, Jr. et al. | |
| 5,753,267 A | 5/1998 | Badylak et al. | |
| 5,762,966 A | 6/1998 | Knapp, Jr. et al. | |
| 5,771,969 A | 6/1998 | Garay | |
| 5,866,414 A | 2/1999 | Badylak et al. | |
| 6,099,567 A | 8/2000 | Badylak et al. | |
| 6,485,723 B1 | 11/2002 | Badylak et al. | |
| 6,576,265 B1 | 6/2003 | Spievack | |
| 6,579,538 B1 | 6/2003 | Spievack | |
| 6,696,270 B2 | 2/2004 | Badylak et al. | |
| 6,783,776 B2 | 8/2004 | Spievack | |
| 6,793,939 B2 | 9/2004 | Badylak | |
| 6,849,273 B2 | 2/2005 | Spievack | |
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 8,361,503 B2 | 1/2013 | Badylak et al. | |
| 8,394,419 B2 | 3/2013 | Borden | |
| 8,691,276 B2 | 4/2014 | Badylak et al. | |
| 8,877,246 B2 | 11/2014 | Everland et al. | |
| 8,927,003 B2 | 1/2015 | Badylak et al. | |
| 9,226,996 B2 | 1/2016 | Moro et al. | |
| 9,277,999 B2 | 3/2016 | Badylak et al. | |
| 9,314,340 B2 | 4/2016 | Badylak et al. | |
| 9,364,580 B2 | 6/2016 | Moro et al. | |
| 9,480,776 B2 | 11/2016 | Badylak et al. | |
| 9,642,937 B2 | 5/2017 | Zhao | |
| 9,814,744 B2 | 11/2017 | Badylak et al. | |
| 9,848,987 B2 | 12/2017 | Badylak et al. | |
| 9,861,662 B2 | 1/2018 | Badylak et al. | |
| 10,004,827 B2 | 6/2018 | Badylak et al. | |
| 10,213,526 B2 | 2/2019 | Badylak et al. | |
| 10,286,119 B2 | 5/2019 | Badylak | |
| 10,729,813 B2 | 8/2020 | Badylak et al. | |
| 10,736,991 B2 | 8/2020 | Badylak et al. | |
| 11,213,545 B2 | 1/2022 | Badylak et al. | |
| 11,291,688 B2 | 4/2022 | Badylak et al. | |
| 11,389,566 B2 | 7/2022 | Ramer et al. | |
| 11,389,569 B2 | 7/2022 | Badylak et al. | |
| 11,406,736 B2 | 8/2022 | Badylak et al. | |
| 11,638,724 B2 | 5/2023 | Badylak et al. | |
| 11,707,485 B2 | 7/2023 | Badylak et al. | |
| 12,161,778 B2 | 12/2024 | Badylak et al. | |
| 12,303,533 B2 | 5/2025 | Badylak et al. | |
| 12,383,243 B2 | 8/2025 | Badylak et al. | |
| 12,440,444 B2 | 10/2025 | Badylak et al. | |
| 2006/0024361 A1 | 2/2006 | Odidi et al. | |
| 2006/0051320 A1 * | 3/2006 | Shameem | A61P 43/00 424/85.4 |
| 2006/0070631 A1 | 4/2006 | Scopton et al. | |
| 2007/0179507 A1 * | 8/2007 | Shah | A61B 17/50 606/113 |
| 2007/0190165 A1 | 8/2007 | Brey et al. | |
| 2007/0224241 A1 | 9/2007 | Stayton et al. | |
| 2008/0260831 A1 | 10/2008 | Badylak et al. | |
| 2012/0020932 A1 | 1/2012 | Yao et al. | |
| 2013/0060008 A1 | 3/2013 | Wang et al. | |
| 2014/0105856 A1 | 4/2014 | Schendel | |
| 2014/0356331 A1 | 12/2014 | Badylak et al. | |
| 2015/0165091 A1 | 6/2015 | Dalecki et al. | |
| 2016/0045552 A1 | 2/2016 | Ramer et al. | |
| 2016/0166735 A1 | 6/2016 | Chang et al. | |
| 2016/0194425 A1 | 7/2016 | Mitra et al. | |
| 2017/0049932 A1 | 2/2017 | Badylak | |
| 2017/0173217 A1 | 6/2017 | Badylak et al. | |
| 2018/0200405 A1 | 7/2018 | Badylak et al. | |
| 2019/0015552 A1 | 1/2019 | Badylak et al. | |
| 2019/0076574 A1 | 3/2019 | Ramer et al. | |
| 2019/0184060 A1 | 6/2019 | Bulman et al. | |
| 2019/0314552 A1 | 10/2019 | Wadsworth et al. | |
| 2021/0244855 A1 | 8/2021 | Badylak et al. | |
| 2021/0268148 A1 | 9/2021 | Badylak et al. | |
| 2023/0071393 A1 | 3/2023 | Badylak et al. | |
| 2024/0226170 A9 | 7/2024 | Badylak et al. | |
| 2025/0228896 A1 | 7/2025 | Badylak | |
| 2025/0235580 A1 | 7/2025 | Badylak | |

FOREIGN PATENT DOCUMENTS

| | | | |
|---|---|---|---|
| CN | 104582747 A | 4/2015 | |
| CN | 106456837 A | 2/2017 | |
| CN | 107921070 A | 4/2018 | |
| CN | 108295311 A | 7/2018 | |
| EP | 0061549 A1 | 3/1985 | |
| JP | S48006021 A | 1/1973 | |
| JP | S57159485 A | 10/1982 | |
| JP | 2009 528090 A | 8/2009 | |
| JP | 2016-520560 A | 7/2016 | |
| JP | 2016-521592 A | 7/2016 | |
| JP | 2017-70221 A | 4/2017 | |
| JP | 2017-511236 A | 4/2017 | |
| JP | 2018-536708 A | 12/2018 | |
| WO | WO-2008107484 A2 * | 9/2008 | A61L 27/3641 |
| WO | WO 2010/032140 A2 | 3/2010 | |
| WO | WO 2014/025312 A1 | 2/2014 | |
| WO | WO 2014/168964 A1 | 10/2014 | |
| WO | WO 2015/143310 A1 | 9/2015 | |
| WO | WO-2015/164728 A1 | 10/2015 | |
| WO | WO 2016/196313 A1 | 12/2016 | |
| WO | WO 2017/079216 A1 | 5/2017 | |
| WO | WO 2017/160878 A1 | 9/2017 | |
| WO | WO 2018/035491 A1 | 2/2018 | |
| WO | WO 2019/122351 A1 | 6/2019 | |
| WO | WO-2019/246442 A1 | 12/2019 | |
| WO | WO-2019/246444 A1 | 12/2019 | |
| WO | WO-2019/246447 A1 | 12/2019 | |
| WO | WO 2020/186082 A1 | 9/2020 | |

OTHER PUBLICATIONS

Hodde, et al., "Effects of sterilization on an extracellular matrix scaffold: part I. Composition and matrix architecture." *J. Mater. Sci. Mater. Med.* 18(4): 537-540, 2007.

Hodde, et al., "Effects of sterilization on an extracellular matrix scaffold: Part II. Bioactivity and matrix interaction." *J. Mater. Sci. Mater. Med.* 18:545-550, 2007.

Hussey, et al., "Extracellular matrix bioscaffolds for building gastrointestinal tissue." *Cellular and Molecular Gastroenterology and Hepatology*, 5.1: 1-13, 2018.

International Search Report and Written Opinion for PCT/US2021/030134, mailed Jul. 23, 2021 (14 pages).

Silva, et al., "Thermoresponsive gel embedded with adipose stem-cell-derived extracellular vesicles promotes esophageal fistula healing in a thermos-actuated delivery strategy." *ACS Nano*, 12.10: 9800-9814, Sep. 25, 2018.

White, et al., "The effects of terminal sterilization upon the biological activity and stiffness of extracellular matrix hydrogels." *Front. Bioeng. Biotechnol.* Conference Abstract: 10th World Biomaterials Congress, Mar. 30, 2016.

Adams et al., "Equine bone marrow-derived mesenchymal stromal cells (BMDMSCs) from the ilium and sternum: Are there differences?" *Equine Veterinary Journal* 45(3)372-375, E-pub Sep. 26, 2012.

Badylak et al., "Esophageal reconstruction with ECM and muscle tissue in a dog model," *The Journal of Surgical Research* 128(1):87-97, Sep. 2005.

Badylak et al., "Resorbable bioscaffold for esophageal repair in a dog model," *Journal of Pediatric Surgery* 35(7):1097-1103, Jul. 2000.

Badylak et al., "Small intestinal submucosa as a large diameter vascular graft in the dog," *The Journal of Surgical Research* 47(1):74-80, Jul. 1989.

(56) References Cited

OTHER PUBLICATIONS

Becton Dickinson, "BD Biosciences, BO Extracellular Matrix Proteins, BO ECM Product Reference Guide," https://www.bd.com/resource.aspx?idx=17649, 2011.
Brown et al., "Macrophage phenotype as a predictor of constructive remodeling following the implantation of biologically derived surgical mesh materials," *Acta Biomaterialia* 8(3):978-87, E-pub Dec. 2, 2011.
Dziki et al., "Solubilized Extracellular Matrix Bioscaffolds Derived from Diverse Source Tissues Differentially Influence Macrophage Phenotype," *Journal of Biomedical Materials Research—Part A* 105(1):138-147, E-pub Sep. 21, 2016.
El-Fiqi et al. "Collagen hydrogels incorporated with surface-aminated mesoporous nanobioactive glass: improvement of physicochemical stability and mechanical properties is effective for hard tissue engineering," *Acta Biomaterialia* 9(12):9508-9521, E-pub Aug. 6, 2013.
Frenguelli et al., "Hepatic differentiation of human induced pluripotent stem cells (iPSC) using 3D human liver extracellular matrix hydrogel," *Journal of Hepatology,* 68(Suppl):S56, Apr. 13, 2018.
Freytes et al., "Preparation and rheological characterization of a gel form of the porcine urinary bladder matrix," *Biomaterials* 229(11): 1630-1637 (Apr. 2008).
Garvin and Vanderburgh "Controlling collagen fiber microstructure in three-dimensional hydrogels using ultrasound," *The Journal of the Acoustical Society of America* 134(2):1491-1502 (Aug. 2013).
Huleihel et al., "Macrophage phenotype in response to ECM bioscaffolds," *Seminars in Immunology* 29:2-13, Feb. 2017.
HUSSEY at al., "Ultrasonic cavitation to prepare ECM hydrogels," *Acta Biomaterialia* 108: 77-86 (e-PUB Apr. 5, 2020).
Hussey et al., "Extracellular matrix-based materials for regenerative medicine," *Nature Reviews Materials* 3:159-173, May 29, 2018.
International Search Report and Written Opinion from parent PCT Application No. PCT/US2020/022433 13 pages (mailed May 29, 2020).
Kakushima et al., "Endoscopic submucosal dissection for gastrointestinal neoplasms," *World Journal of Gastroenterology* 14(19):2962-2967, May 21, 2008.
Keane et al., "Tissue-specific effects of esophageal extracellular matrix," *Tissue Engineering Part A* 21(17-18):2293-2300, E-pub Aug. 12, 2015.
Kim et al., "Application of ultrasonic treatment to extraction of collagen from the skins of sea bass Lateolabrax japonicus," *Fisheries Science* 79(5):849-856, Jul. 6, 2013.
Kornmuller et al., "Fabrication of extracellular matrix-derived foams and microcarriers as tissue-specific cell culture and delivery platforms," *Journal of Visualized Experiments* 122:55436 (Apr. 2017).
Lange et al., "Pilot study of a novel vacuum-assisted method for decellularization of tracheae for clinical tissue engineering applications," *Journal of Tissue Engineering and Regenerative Medicine* 11(3):800-811, E-pub Feb. 17, 2015.
Li et al., "Ultrasonic irradiation in the enzymatic extraction of collagen," *Ultrasonics Sonochemistry* 16(5): 605-609 (Dec. 31, 2009).
Loneker et al., "Solubilized liver extracellular matrix maintains primary rat hepatocyte phenotype in-vitro," *Journal of Biomedical Materials Research Part A* 104(4):957-965, E-pub Jan. 13, 2016.
Luan, "Separation and Characterization of Protein Components in Bovine Tendon Acellular Matrix Materials," *Chinese Master's Theses Full-Text Database, Engineering Technology I,* issue 1 (Jan. 15, 2021), in Chinese with English Abstract.
Mase et al., "Clinical application of an acellular biologic scaffold for surgical repair of a large, traumatic quadriceps femoris muscle defect," *Orthopedics* 33(7):511, Jul. 13, 2010.
Medberry et al., "Hydrogels derived from central nervous system extracellular matrix," *Biomaterials* 34(4):1033-1040, E-pub Nov. 16, 2012.
Reing et al., "The effects of processing methods upon mechanical and biologic properties of porcine dermal extracellular matrix scaffolds," *Biomaterials* 31(33):8626-8633, E-pub Aug. 21, 2010.
Saldin et al., "Extracellular matrix hydrogels from decellularized tissues: Structure and function," *Acta Biomaterialia* 49:1-15, E-pub Dec. 1, 2016.
Shen et al., "Preparation and characterization of a gene-activated matrix mimicking extracellular matrix," *Acta Pharmaceutica Sinica,* 52(11): 1748-1755 (Nov. 12, 2017), in Chinese with English Abstract.
Sicari et al., "The promotion of a constructive macrophage phenotype by solubilized extracellular matrix," *Biomaterials* 35(30):8605-8612, E-pub Jul. 16, 2014.
Spang et al., "Extracellular matrix hydrogel therapies: In vivo applications and development," *Acta Biomaterialia* 68:1-14, E-pub Dec. 20, 2017.
Thornton et al., "Healing in the gastrointestinal tract," *The Surgical Clinics of North America* 77(3):549-573, Jun. 1997.
Tosh et al., "Determination of the maximum gelation temperature in gelatin gels," *Applied Physics Letters* 84(21):4242-4244, May 24, 2004.
Uraoka et al., "Submucosal injection solution for gastrointestinal tract endoscopic mucosal resection and endoscopic submucosal dissection," *Drug Design, Development and Therapy* 2:131-138, Feb. 6, 2009.
Uriel et al., "The role of adipose protein derived hydrogels in adipogenesis," *Biomaterials* 29(27):3712-3719, E-pub Jun. 24, 2008.
Uriel et al., "Extraction and assembly of tissue-derived gels for cell culture and tissue engineering," *Tissue Engineering: Part C* 15(3): 309-321 (2009).
Ventura et al., "In-vitro and in-vivo evaluation of hemostatic potential of decellularized ECM hydrogels," *Materials Letters* 232: 130-133 (available on-line Aug. 6, 2018).
Voytik-Harbin et al., "Small intestinal submucosa: A tissue-derived extracellular matrix that promotes tissue-specific growth and differentiation of cells in vitro," *Tissue Engineering* 4(2):157-174, Jun. 1, 1998.
Wang et al., "Sonication-induced gelation of silk fibroin for cell encapsulation," *Biomaterials* 29(8): 1054-1064 (Mar. 2008).
Wolf., "Polypropylene surgical mesh coated with extracellular matrix mitigates the host foreign body response," *Journal of Biomedical Materials Research Part A* 102(1):234-246, E-pub Jul. 19, 2013.
Wu et al., "Therapeutic effect of lung ECM hydrogel on radiation-induced lung injury in rats," *China Journal of Modern Medicine* 29: 12 (Jun. 27, 2019)(with machine English language translation).
Zoulim, "Inhibition of hepatitis B virus gene expression: A step towards functional cure," *J. Hepatol.* 68: 386-388 (2018).
Crum et al., "TU2052: Development of a colloidal, extracellular matrix hydrogel for the operative management of simple and complex anorectal fistulas," SSAT *Abstracts*, Gastroenterology 158(6):Supplement 1, S-1601 (May 2020).
Dziki et al., "Bioscaffold-Mediated Mucosal Remodeling Following Short-Segment Colonic Mucosal Resection," *Journal of Surgical Research* 218:353-360, Oct. 2017.
Faust et al., "Urinary Bladder Extracellular Matrix Hydrogels and Matrix-Bound Vesicles Differentially Regulate Central Nervous System Neuron Viability and Axon Growth and Branching," *Journal of Biomaterials Applications* 31(9):1277-1295, 2017.
Hussey et al., "The Extracellular Matrix of the Gastrointestinal Tract: A Regenerative Medicine Platform," *Nature Reviews Gastroenterology & Hepatology* 14:540-552, e-Pub Jul. 12, 2017.
Keane et al., "Preparation and Characterization of a Biologic Scaffold and Hydrogel Derived from Colonic Mucosa," *J Biomed Mater Res* Part B 105B:291-306, 2015.
Keane et al., "Restoring Mucosal Barrier Function and Modifying Macrophage Phenotype with an Extracellular Matrix Hydrogel: Potential Therapy for Ulcerative Colitis," *Journal of Crohn's and Colitis*: 360-368, e-Pub Sep. 10, 2017.
Meng et al., "Solubilized Extracellular Matrix from Brain and Urinary Bladder Elicits Distinct Functional and Phenotypic Responses in Macrophages," *Biomaterials* 46:131-140, e-Pub Jan. 24, 2015.
Molina et al., "Comparison of the Host Macrophage Response to Synthetic and Biologic Surgical Meshes Used for Ventral Hernia Repair," *Journal of Immunology and Regenerative Medicine* 3:13-25, e-Pub Dec. 26, 2018.

(56) References Cited

OTHER PUBLICATIONS

Saldin et al., "Extracellular Matrix Degradation Products Downregulate Neoplastic Esophageal Cell Phenotype," *Tissue Engineering* Part A 25(5 and 6): 487-496, e-Pub Feb. 26, 2019.
Shaffiey et al., "Intestinal Stem Cell Growth and Differentiation on a Tubular Scaffold with Evaluation in Small and Large Animals," *Regenerative Medicine* 11(1):45-61, e-Pub Sep. 18, 2015.

* cited by examiner

40mg/ml Trehalose

20mg/ml Trehalose

0mg/ml (control)

Modulus G' (Pa)
4000
3000
2000
1000
0
15/15
30
35
40
45
eBeam dose

Storage Modulus (Pa)
15000
10000
5000
0
Trehalose (mg/mL)
Colloid (%)
20 40
2%
20 40
5%
20 40
10%

FIG. 7A
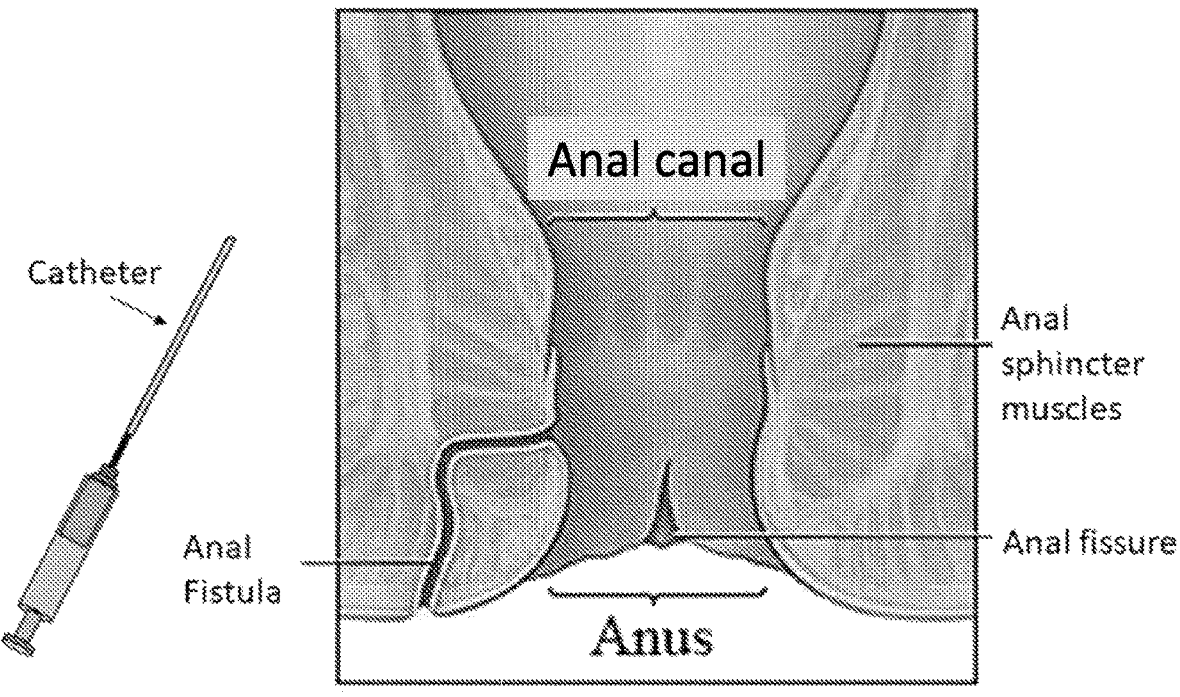
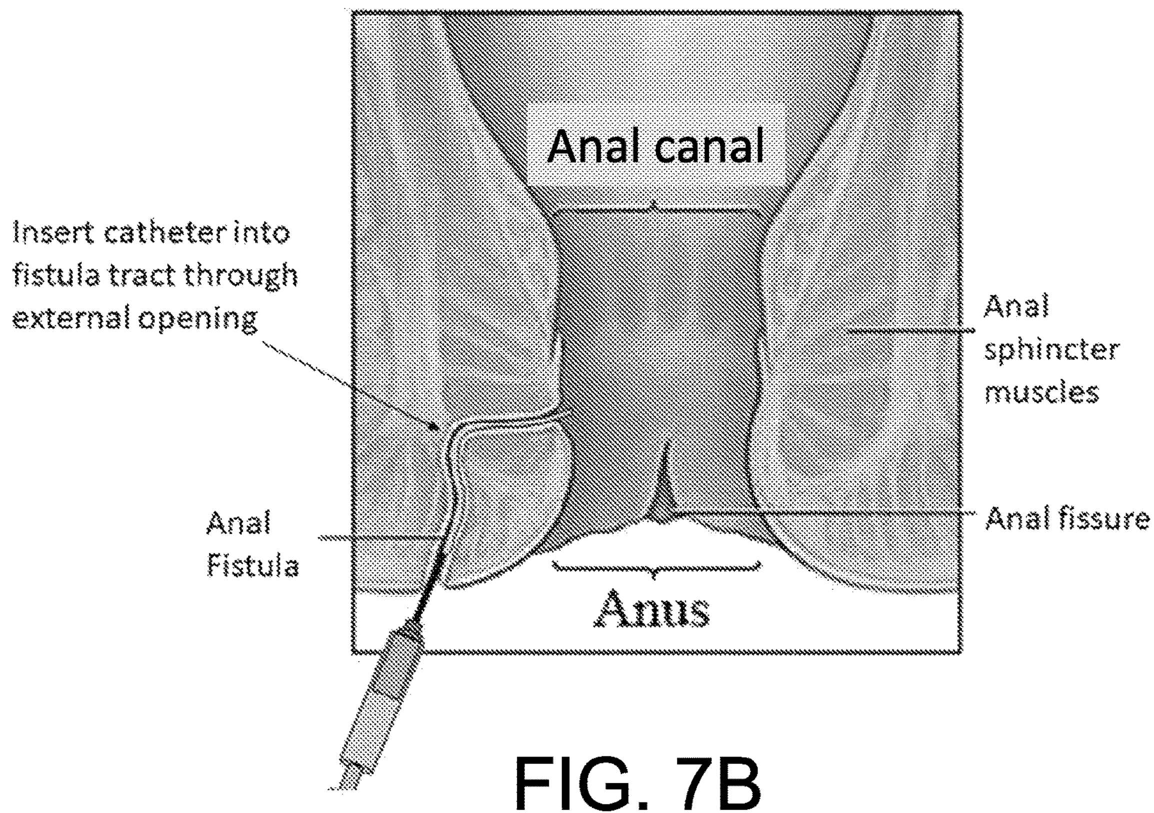
FIG. 7B

METHODS FOR PREPARATION OF A TERMINALLY STERILIZED HYDROGEL OR COLLOIDAL SUSPENSION DERIVED FROM EXTRACELLULAR MATRIX, AND USES THEREOF

CROSS REFERENCE TO RELATED APPLICATION

This is a § 371 U.S. national stage of International Application No. PCT/US2021/030134, filed Apr. 30, 2021 which claims the benefit of U.S. Provisional Application No. 63/077,084, filed Sep. 11, 2020, which is incorporated by reference herein.

STATEMENT OF GOVERNMENT SUPPORT

This invention was made with government support under grant number W81XWH-19-9-0012 awarded by the U.S. Army Medical Research and Materiel Command (ARMY/MRMC). The government has certain rights in the invention.

FIELD OF THE DISCLOSURE

This relates to the field of hydrogels, specifically to the use of a mammalian acoustic extracellular matrix (ECM) hydrogel for repairing a fistula, such as, but not limited to, an anal fistula.

PARTIES TO JOINT RESEARCH AGREEMENT

This invention was made under a research agreement between the University of Pittsburgh—Of the Commonwealth System of Higher Education and ECM Therapeutics, Inc., which was executed prior to the filing date of the present application.

BACKGROUND

Anorectal fistulas are pathologic connections between the epithelial surface of the anal canal and the skin of the perineum and perianal region. Anorectal fistulas represent a significant procedural burden for gastroenterology and colorectal surgery as there are different approaches to management. Using current methods, procedural outcomes are frequently poor. Regardless of management, anorectal fistulas present with significant implications for patient morbidity and mortality as fistula sequelae can range from social embarrassment to frank infection and sepsis. In addition, high recurrence rates, surgical complication rates, and subsequent procedures to manage anorectal fistulas significantly reduce patient quality of life and increase health care expense. Thus, there is a need for new compositions and methods for the treatment of these fistulas and other fistulas.

SUMMARY OF THE DISCLOSURE

A method is disclosed for treating a fistula in a subject. In some embodiments, the method includes administering locally to the fistula in the subject an effective amount of a composition comprising a mammalian acoustic extracellular matrix (ECM) hydrogel, wherein a) the mammalian acoustic ECM hydrogel is thermoreversible, wherein the mammalian acoustic ECM hydrogel is in a gel phase at temperatures below about 37° C. and transitions to a liquid phase at temperatures above about 37° C., b) the mammalian acoustic ECM hydrogel includes solubilized ECM at a concentration of about 0.1 mg/ml to about 1,000 mg/ml, and c) the composition has a storage modulus (G') to loss modulus (G") ratio in the range of about 6:1 to about 12:1 at 37° C. In some non-limiting embodiments, the fistula is an anal fistula.

In some embodiments, a composition is disclosed that includes i) a mammalian acoustic extracellular matrix (ECM) hydrogel, wherein: a) the mammalian acoustic ECM hydrogel is thermoreversible, wherein the mammalian acoustic ECM hydrogel is in a gel phase at temperatures below about 37° C. and transitions to a liquid phase at temperatures above about 37° C., b) mammalian acoustic ECM hydrogel comprises solubilized ECM at a concentration of about 0.1 mg/ml to about 1,000 mg/ml, c) the composition has a storage modulus (G') to loss modulus (G") ratio of about 6:1 to about 12:1 at 37° C. The composition also includes ii) 0.1 mg/ml to about 700 mg/ml trehalose; and iii) about 1 to about 30% (weight per volume) of comminuted ECM that is not solubilized in the hydrogel. In some non-limiting embodiments, the composition is used in a method to treat a fistula in a subject. In some non-limiting embodiments, the fistula is an anal fistula.

In further embodiments, disclosed is a composition comprising a mammalian acoustic extracellular matrix (ECM) hydrogel for use in treating a fistula in a subject. In these compositions: a) the mammalian acoustic ECM hydrogel is thermoreversible, wherein the mammalian acoustic ECM hydrogel is in a gel phase at temperatures below about 37° C. and transitions to a liquid phase at temperatures above about 37° C., b) the mammalian acoustic ECM hydrogel comprises solubilized ECM at a concentration of about 0.1 mg/ml to about 1,000 mg/ml, and c) the composition has a storage modulus (G') to loss modulus (G") ratio of about 6:1 to about 12:1 at 37° C. In some non-limiting examples, the fistula is an anal fistula.

The foregoing and other features and advantages of the invention will become more apparent from the following detailed description of several embodiments which proceeds with reference to the accompanying figures.

BRIEF DESCRIPTION OF THE FIGURES

FIGS. 7A-7E: Dermis acoustic hydrogel can be used to fill a fistula tract. A 4 cm transphincteric fistula tract was made in a pig. 100 mg/ml dermal acoustic gel was administered by inserting a catheter through the external opening of the tract (A) and guided toward the internal opening (B). Then the catheter was slowly retracted while injecting gel into the tract (C, D). (E) Photograph of the fistula tract filled dermis acoustic gel. The gel is the dark green spot at approximately 11 o'clock on the anus.

DETAILED DESCRIPTION OF SEVERAL EMBODIMENTS

Figure 1:
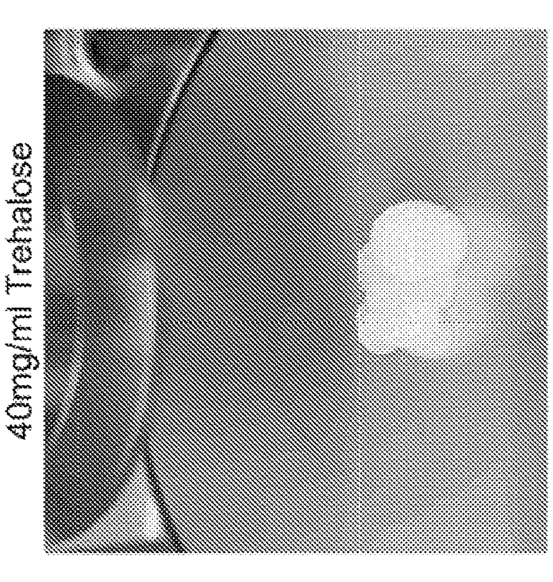
FIG. 1: Trehalose prevents acoustic ECM hydrogel aggregation after E-beam sterilization. The ultrasonic cavitation method was used to prepare 100 mg/ml dermal ECM (dECM) hydrogels with 20 or 40 mg/ml trehalose. A 100 mg/ml dermal ECM hydrogel prepared without trehalose served as a control (left panel). The data show that the addition of trehalose at a concentration of 20-40 mg/ml (middle and left panels) prevented the dermal ECM hydrogels from forming aggregates after sterilization with 35 kGy E-beam. The composition without trehalose is not adherent and forms small aggregates or clumps, whereas the compositions containing trehalose form a uniform, adherent composition with a generally smooth texture.
Figure 1:
Figure 1:
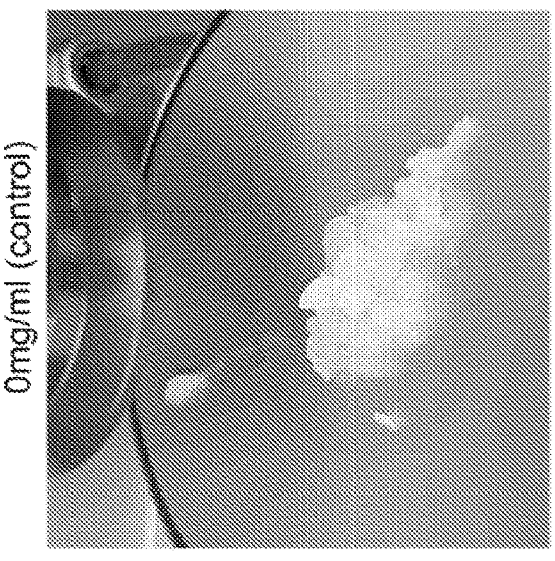

Anorectal fistulas are pathologic connections between the epithelial surface of the anal canal and the skin of the perineum and perianal region. Anorectal fistulas represent a significant procedural burden for gastroenterology and colorectal surgery as there is substantial controversy in the approach to management and procedural outcomes are poor. Regardless of management, anorectal fistulas present with significant implications for patient morbidity and mortality as fistula sequelae can range from social embarrassment to frank infection and sepsis. In addition, high recurrence rates, surgical complication rates, and subsequent procedures to manage anorectal fistulas significantly reduce patient quality of life and increase health care expense. Disclosed is space-filling, pro-remodeling, colloidal hydrogel composition that can be used for the treatment of anal fistulas.

It is disclosed herein that compositions including mammalian acoustic ECM hydrogels demonstrated clinical efficacy for the management of unregulated inflammation and promotion of wound healing in anal fistulas. As disclosed in the examples, ECM was exposed to ultrasonication, and used to produce compositions for use in treating anal fistulae. In vitro results demonstrate that the disclosed compositions can be sterilized and used as a stiff biomaterial capable of filling fistula tracts of complex architecture at body temperature, can modulate macrophages toward a pro-remodeling phenotype (Fizz+), and have hemostatic properties. The disclosed compositions maintain rigidity in ex vivo tracts and did not degrade or leak out of the tract at body temperature.

In a post-mortem, ex-vivo porcine fistula model, the compositions were capable of filling tracts without leakage at body temperature. The combined space-filling, anti-inflammatory, and hemostatic properties made these compositions of use for treatment of simple and complex anorectal fistulas. The ease of injection, sterility, and stability allow the disclosed compositions to be used "off-the-shelf" in both surgical and out-patient settings. The disclosed compositions improve healing, mitigate operative bleeding, and reduce complications and reduce recurrence in the management of anorectal fistulas.

Terms

Unless otherwise noted, technical terms are used according to conventional usage. Definitions of common terms in molecular biology can be found in Krebs et al (Eds.), *Lewin's Genes XII*, published by Jones & Bartlett Publishers, 2017; and Meyers et al. (eds.), *The Encyclopedia of Cell Biology and Molecular Medicine*, published by Wiley-VCH in 16 volumes, 2008; and other similar references.

In order to facilitate review of the various embodiments of this disclosure, the following explanations of specific terms are provided:

Acid Protease: An enzyme that cleaves peptide bonds, wherein the enzyme has increased activity of cleaving peptide bonds in an acidic pH. For example and without limitation, acid proteases can include pepsin and trypsin.

Anal Fistula: A small tunnel connecting the anal canal to the perianal skin. The majority are associated with an anorectal abscess. Anal fistulas can result from an infection in the anal glad that spreads to the skin. Symptoms include pain, swelling and discharge of blood or pus from the anus. There are several types of anal fistulas, including intersphincteric (most common), trans-sphincteric, extra-sphincteric and supra-sphincteric (least common).

Antibiotic: A compound or substance that kills or substantially slows down the growth of bacteria, fungus or any other microbe. An "antibacterial" is a compound or substance that kills or substantially slows the growth of bacteria.

Antibacterial antibiotics are commonly classified based on their mechanism of action, chemical structure, or spectrum of activity. Most target bacterial functions or growth processes. Those that target the bacterial cell wall (for example, penicillins and cephalosporins) or the cell membrane (for example, polymixins), or interfere with essential bacterial enzymes (for example, quinolones and sulfonamides) are bactericidal. Those that target protein synthesis (for example, aminoglycosides, macrolides, and tetracyclines) are generally bacteriostatic. Further categorization is based on their target specificity.

"Narrow-spectrum" antibacterial antibiotics target specific types of bacteria, such as Gram-negative or Gram-positive bacteria. "Broad-spectrum antibiotics" affect a number of different types of bacteria. Antibacterial agents also include cyclic lipopeptides (such as daptomycin), glycylcyclines (such as tigecycline), and oxazolidinones (such as linezolid).

Topical antibiotics are antibiotics that are applied to a body surface, such as the skin or eye. Topical antibiotics are often formulated in an ointment or a cream, and contain active agents such as macrolide antibiotic (such as erythromycin), a sulfa antibiotic (such as sulfacetamide), a cyclic peptide (such as bacitracin a polymyxin) a psuedomonic acid (such as mupirocin), an aminoglycoside (such as neomycin), or a quinolone (such as ciprofloxacin or ofloxacin), a nitroimidazole (such as metronidazloe), or a combination of drugs (such as bacitracine/polymyxin or neomycin/polymyxin B/bacitracin).

Biocompatible: Any material, that, when implanted in a mammalian subject, does not provoke an adverse response in the subject. A biocompatible material, when introduced into an individual, is able to perform its intended function, and is not toxic or injurious to that individual, nor does it induce immunological rejection of the material in the subject.

Centrifugation: The process whereby a centrifugal force is applied to a mixture, whereby more-dense components of the mixture migrate away from the axis of the centrifuge relative to other less-dense components in the mixture. The force that is applied to the mixture is a function of the speed of the centrifuge rotor, and the radius of the spin. In most applications, the force of the spin will result in a precipitate (a pellet) to gather at the bottom of the centrifuge tube, where the remaining solution is properly called a "supernate" or "supernatant." In other similar applications, a density-based separation or "gradient centrifugation" technique is used to isolate a particular species from a mixture that contains components that are both more dense and less dense than the desired component.

During the circular motion of a centrifuge rotor, the force that is applied is the product of the radius and the angular velocity of the spin, where the force is traditionally expressed as an acceleration relative to "g," the standard acceleration due to gravity at the Earth's surface. The centrifugal force that is applied is termed the "relative centrifugal force" (RCF), and is expressed in multiples of "g."

Comminute (comminution and comminuting): The process of reducing larger particles into smaller particles, including, without limitation, by grinding, blending, shredding, slicing, milling, or cutting. ECM can be comminuted while in any form, including, but not limited to, hydrated forms, frozen, air-dried, lyophilized, powdered, or sheet-form. "Comminuted ECM" includes intact collagen. Comminuted ECM has not been subjected to ultrasound.

Contacting: Placement in direct physical association, which can be in solid or liquid form.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-α, interleukin (IL)-6, IL-10, IL-12, transforming growth factor, and interferon-γ.

Diagnosis: The process of identifying a disease by its signs, symptoms and results of various tests. The conclusion reached through that process is also called "a diagnosis." Forms of testing commonly performed include blood tests, medical imaging, and biopsy.

Extracellular Matrix (ECM): A natural acellular scaffolding for cell growth. Natural ECMs (ECMs found in multicellular organisms, such as, but not limited to, mammals and humans) are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestinal submucosa (SIS), urinary bladder matrix (UBM), esophagus (E) and liver stroma ECM each differ in their overall structure and composition due to the unique cellular niche needed for each tissue. An intact "extracellular matrix" and "intact ECM" is an extracellular matrix that retains activity of its structural and non-structural biomolecules, including, but not limited to, collagens, elastins, laminins, glycosaminoglycans, proteoglycans, antimicrobials, chemoattractants, cytokines, and growth factors.

The structure and/or activity of the biomolecules within the ECM can be altered or removed chemically or mechanically, for example, by cross-linking and/or by dialyzing the ECM. Intact ECM essentially has not been enzymatically digested, cross-linked and/or dialyzed, meaning that the ECM has not been subjected to a digestion, dialysis and/or a cross-linking process, or conditions other than processes that occur naturally during storage and handling of ECM prior to solubilization. Thus, ECM that is substantially cross-linked and/or dialyzed (in anything but a trivial manner which does not substantially affect the gelation and functional characteristics of the ECM in its uses described herein) is not considered to be "intact." "Acellular" refers to ECM produced from a source tissue that has been treated to remove the cells such that the ECM remains. Decellularized tissue is used to produce ECM hydrogels.

Fistula: An abnormal connection or passageway between organs or vessels that normally do not connect. Fistulas can develop in various parts of the body in connection with diseases in the circulatory-, respiratory-, digestive-, genitourinary-, musculoskeletal systems and connective tissue beside congenital malformations, deformations and chromosomal abnormalities. The type of the fistula can be blind with only one open end, it can be complete with both an external and an internal opening or incomplete with an external skin opening, which does not connect to any internal organs. The most common form of fistula is in the form of a tube with the possibility to have multiple branches.

Gel: A state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (for example, the shape is discrete enough to maintain three dimensions on a two dimensional surface). "Gelation time," also referred to as "gel time," refers to the time it takes for a composition to become non-flowable under modest stress.

Gelation: The formation of a gel from a sol.

Hemostasis: The inhibition or halting of hemorrhage.

Hydrogel: A network of polymer chains that are hydrophilic, sometimes found as a colloidal gel in which water is the dispersion medium. Hydrogels are highly absorbent natural or synthetic polymeric networks. Hydrogels also possess a degree of flexibility similar to natural tissue. An "acoustic" hydrogel, such as an acoustic ECM hydrogel, is produced using ultrasound energy. The characteristics of these hydrogels are disclosed herein. For a hydrogel, the G' (storage modulus) is typically about an order of magnitude greater than the G" (loss modulus). An "enzymatic" ECM hydrogel is produced by enzymatically digested ECM. The viscosity of an enzymatic hydrogel increases when warmed to physiological temperatures approaching about 37° C. For example, an enzymatic hydrogel is formed from an injectable solution at temperatures lower than 37° C. which forms a gel at a physiological temperature of 37° C.

Isolated: An "isolated" biological component (such as extracellular matrix) has been substantially separated, produced apart from, or purified away from other biological components, cells or the organism in which the component naturally occurs, i.e., live cells, other chromosomal and extrachromosomal DNA and RNA, and proteins. ECM that has been "isolated" thus includes ECM that is removed from tissue by standard purification methods. An isolated ECM has been separated from cells that produce the ECM.

Isotonic Buffered Solution: A solution that is buffered to a pH between 7.2 and 7.8 and that has a balanced concentration of salts to promote an isotonic environment.

Macrophage: A type of white blood cell that phagocytoses and degrades cellular debris, foreign substances, microbes, and cancer cells. In addition to their role in phagocytosis, these cells play an important role in development, tissue maintenance and repair, and in both innate and adaptive immunity in that they recruit and influence other cells including immune cells such as lymphocytes. Macrophages can exist in many phenotypes, including phenotypes that have been referred to as M1 and M2, also called "M1-like" and "M2-like." Macrophages that perform primarily pro-inflammatory functions are called M1 macrophages (CD86+/CD68+), whereas macrophages that decrease inflammation and encourage and regulate tissue repair are called M2 macrophages (CD206+/CD68+). The markers that identify the various phenotypes of macrophages vary among species. It should be noted that macrophage phenotype is represented by a spectrum that ranges between the extremes of M1 and M2. The marker Fizz-1, (see Raes et al., Dev. Immunol. 9: 151-159, 2002, incorporated herein by reference) identifies those macrophages considered to be remodeling, i.e., M2 macrophages.

Mammal: This term includes both human and non-human mammals. Similarly, the term "subject" includes both human and veterinary subjects.

Preventing or treating a disease: "Preventing" a disease refers to inhibiting the partial or full development of a disease, for example in a person who is known to have a predisposition to a disease. "Treatment" refers to a therapeutic intervention that ameliorates a sign or symptom of a disease or pathological condition after it has begun to develop. In several embodiments, treatment refers to a reduction in incontinence, closing at least a portion of a fistula, or a decrease of symptoms of an anal fistula.

Solubilized ECM: ECM that has been treated with ultrasonic cavitation thereby causing micro-structural changes by physical disruption of protein aggregates.

Therapeutic agent: Used in a generic sense, it includes treating agents, prophylactic agents, and replacement agents. "Treatment" or "treating" means providing a substance, such as a disclosed composition, to a patient in an amount sufficient to measurably affect a biological parameter, such as to increase hemostasis or tissue growth.

Therapeutically effective amount: A "therapeutically effective amount" of a composition means an amount effective, when administered to a patient, to provide a therapeutic benefit such as an amelioration of symptoms, reduced decrease progression, or cause disease regression. A quantity of a composition is sufficient to achieve a desired effect in a subject being treated, such as a subject with an anal fistula. A therapeutically effective amount can be administered locally, such as to the anal fistula. In addition, an effective amount can be administered in a single dose, or in several doses at different times. The effective amount will be dependent on the preparation applied, the subject being treated, the severity and type of the affliction, such as the type of fistula. The compositions of use in the methods disclosed herein have equal applications in medical and veterinary settings. Therefore, the general term "subject" or "patient" is understood to include all animals, including, but not limited to, humans or veterinary subjects, such as other primates, dogs, cats, horses, and cows.

Thermoreversible hydrogel: Hydrogel formed due to entanglement of polymer chains wherein the viscosity changes at a characteristic temperature of gelation. The disclosed acoustic ECM hydrogels are thermoreversible hydrogels that show gelation (sol to gel transition) upon cooling.

Topical application: A topically applied agent is applied only in a specific area, and not throughout the body. In particular examples the composition is applied to the skin or the eye in an area where hemostasis is desired. For example the pharmaceutical composition can be applied in a topical preparation to a wound, such as an epithelial wound or defect, for example a traumatic or surgical wound, such as a skin or corneal abrasion or surgical incision.

Ultrasonication: The process of exposing ultrasonic waves with a frequency higher than 20 kHz.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. "About" indicates within 5% of a listed value. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Extracellular Matrix (ECM)

Any type of extracellular matrix can be used to produce a mammalian acoustic ECM hydrogel (see U.S. Pat. Nos. 4,902,508; 4,956,178; 5,281,422; 5,352,463; 5,372,821; 5,554,389; 5,573,784; 5,645,860; 5,771,969; 5,753,267;

5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666 related to ECM). In certain embodiments, the ECM is isolated from a vertebrate animal, for example and without limitation, from a mammal including, but not limited to, humans, monkeys, horses, pigs, cows and sheep. In specific non-limiting examples, the ECM is porcine.

ECM can be derived from any organ or tissue, including without limitation, urinary bladder, intestine (such as small intestine or large intestine), heart, kidney, uterus, brain, blood vessel, lung, bone, muscle, pancreas, stomach, spleen, adipose tissue, muscle tissue, liver, esophagus, placenta, and dermis. The ECM can be obtained from a cell culture. In one embodiment, the ECM is isolated from a urinary bladder. In another embodiment, the ECM is from an esophagus. In another embodiment, the ECM is from dermis. In another embodiment, the ECM is from small intestinal submucosa (SIS). The ECM may or may not include the basement membrane portion of the ECM. In certain embodiments, the ECM includes at least a portion of the basement membrane. A tissue can be decellularized to remove cells and cellular material, e.g., from the source tissue or organ, to produce an ECM. It desirable to use a decellularized material prevent an immune response, such as when ECM is implanted in a subject, for example, as a component of a hydrogel disclosed herein. Removal of cellular material, such as when using ECM to form a hydrogel, prevents such an immune response.

U.S. Pat. No. 8,361,503 (incorporated herein by reference) discloses preparation of a urinary bladder ECM, such as porcine bladder. ECM is prepared by abrading bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. In some embodiments, perforation of the submucosa is prevented. After these tissues are removed, the resulting ECM consists mainly of the tunica submucosa.

The production of hydrogels from dermal ECM is disclosed in Wolf et al., Biomaterials 33: 7028-7038, 2012, incorporated herein by reference. The production of ECM from esophageal tissue is disclosed, for example, in Badylak et al. J Pediatr Surg. 35(7):1097-103, 2000 and Badylak et al., J Surg Res. 2005 September; 128(1):87-97, 2005, both incorporated herein by reference. U.S. Pat. No. 6,893,666, incorporated herein by reference, discloses production of ECM from urinary bladder, skin, esophagus and small intestine. ECM can be produced from any of these tissues.

Commercially available ECM preparations can also be used. In one embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (Acell Corporation; Jessup, Md.).

Tissue for preparation of ECM can be harvested in a large variety of ways and once harvested, a variety of portions of the harvested tissue may be used. ECM has also been prepared from the esophagus and small intestine, see, for example, Keane et al., Tissue Eng. Part A, 21(17-18): 2293-2300, 2015, incorporated herein by reference. Esophageal ECM can be prepared by mechanically separating the mucosa and submucosa from the muscularis externa and digesting the mucosal layers in a buffer including trypsin, followed by exposure to sucrose, TRITON-X100®, deoxycholic acid, peracetic acid and DNAse. Small intestine submucosa (SIS) can be prepared by mechanically removing the superficial layers of the tunica mucosa, tunica serosa, and tunica muscularis externa from the intact small intestine, leaving the submucosa, muscularis mucosa, and basilar stratum compactum intact. The SIS is then treated with peracetic acid. Exemplary protocols are provided in Keane et al. Dermal hydrogels can be produced, for example, as disclosed in Wolf et al, *J Biomed Mater Res A.* 2013. 35(25):6838-49. PMID: 23873846. PMCID: 3808505, incorporated herein by reference.

In one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa can be removed by mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa can also be dissociated by soaking the tissue in a de-epithelializing solution, for example and without limitation, hypertonic saline. The resulting UBM comprises basement membrane of the tunica mucosa and the adjacent tunica propria, which is further treated with peracetic acid, lyophilized and powdered, see U.S. Pat. No. 8,361,503, incorporated herein by reference.

Dermis sections can be used for the preparation of the ECM hydrogels, see PCT Application No. 2015/15164728, incorporated herein by reference. In a specific non-limiting example, the dermis can be decellularized with 0.25% Trypsin/1% TRITON-X®-100 (i.e. no SDS) on a vortex shaker at 300 RPM at room temperature in the following solutions: 0.25% trypsin for 6 hours, lx; deionized water, 15 minutes, 3×; 70% ethanol, 10 to 12 hours, lx; 3% $H_2O_2$, 15 minutes, 1×; deionized water, 15 minutes, 2×; 1% TRITON-X®-100 in 0.26% EDTA/0.69% Tris, 6 hours, 1×, and then overnight, 1×; deionized water, 15 minutes, 3×; 0.1% peracetic acid/4% ethanol, 2 hours, 1×; PBS, 15 minutes, 2×; and finally deionized water, 15 minutes, 2×. Dermis sheets are then lyophilized and subsequently reduced to particulate form using a Waring blender and a Wiley Mill with a #20 mesh screen.

In some embodiments, the epithelial cells can be delaminated by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

In some embodiments, the ECM itself can be sterilized by any number of standard techniques, including, but not limited to, exposure to peracetic acid, low dose gamma radiation, gas plasma sterilization, ethylene oxide treatment or electron beam treatment. More typically, sterilization of ECM is obtained by soaking in 0.1% (v/v) peracetic acid, 4% (v/v) ethanol, and 95.9% (v/v) sterile water for two hours. The peracetic acid residue is removed by washing twice for 15 minutes with PBS (pH=7.4) and twice for 15 minutes with sterile water. ECM material can be sterilized by propylene oxide or ethylene oxide treatment, gamma irradiation treatment (0.05 to 4 mRad), gas plasma sterilization, peracetic acid sterilization, or electron beam treatment. The ECM can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. As disclosed in U.S. Pat. No. 8,361,503, ECM is disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water.

Generally, following isolation of the tissue of interest, decellularization is performed by various methods, for example and without limitation, exposure to hypertonic saline, peracetic acid, TRITON-X® or other detergents. Sterilization and decellularization can be simultaneous. For example and without limitation, sterilization with peracetic acid, described above, also can be used for decellularization. ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state.

Mammalian ECM is also commercially available. These include AVITENE™, MICROMATRIX® and XENMATRIX™. These commercially available products can also be used to produce a mammalian acoustic ECM hydrogel.

Acoustic ECM Hydrogels and Compositions for Use

Compositions are disclosed herein that can be administered locally to a fistula, for example, an anal fistula, and thus used for treatment. The compositions include a mammalian acoustic extracellular matrix (ECM) hydrogel that is thermoreversible, and is in a gel phase at temperatures below about 37° C. and transitions to a liquid phase at temperatures above about 37° C. The mammalian acoustic ECM hydrogel comprises solubilized ECM at a concentration of about 0.1 mg/ml to about 1,000 mg/ml, and the composition has a storage modulus (G') to loss modulus (G") ratio in the range of about 6:1 to about 12:1 at 37° C. The composition can also include a radioprotectant, such as trehalose at a concentration of 0.1 mg/ml to 700 mg/ml. Mammalian acoustic ECM hydrogels are disclosed, for example, in PCT Publication No. WO2020/186082, which is incorporated herein by reference.

These acoustic ECM hydrogels can be made from any mammalian ECM disclosed above. The source of ECM can be, for example, porcine, bovine, human or ovine. In specific, non-limiting example, the ECM is porcine ECM. In other non-limiting examples, the ECM is urinary bladder ECM, small intestinal submucosal ECM, esophageal EMC, tracheal ECM, liver ECM, or dermal ECM. In one embodiment, the ECM is urinary bladder ECM. In another embodiment, the ECM is dermal ECM. In yet another embodiment, the ECM is small intestinal submucosal ECM.

In some embodiments, the mammalian acoustic ECM hydrogel includes solubilized ECM at a concentration of greater than about 0.1 mg/ml. The mammalian acoustic ECM hydrogel can include solubilized ECM at a concentration of about 0.1 mg/ml to about 1,000 mg/ml. Suitable concentrations also include about 1 mg/ml to about 1,000 mg/ml, about 1 mg/ml to about 100 mg/ml, about 10 mg/ml to 100 mg/ml, about 10 mg/ml to about 200 mg/ml, about 100 mg/ml to about 500 mg/ml, about 50 mg/ml to about 150 mg/ml, about 20 mg/ml to about 70 mg/ml, or about 40 mg/ml to about 66 mg/ml of solubilized ECM. In one embodiment, the ECM hydrogel can include solubilized ECM at a concentration of about 20 mg/ml to about 100 mg/ml. The mammalian acoustic ECM hydrogel can include solubilized ECM at a concentration of about 10 mg/ml to about 500 mg/ml in the liquid, such as the buffer. The mammalian acoustic ECM hydrogel can include 10, 25, 30, 35, 40, 45, 50, 55, 60, 65, 70, 75, 80, 85, 90, 95, 100, 105, 110, 115, 120, 125, 130, 135, 140, 150, 155, 160, 165, 170, 175, 180, 185, 190, 195, and 200 mg/ml solubilized ECM. Exemplary concentrations include about 20 mg/ml, 40 mg/ml, 66 mg/ml, 70 mg/ml, and 150 mg/ml solubilized ECM. In one non-limiting example, the mammalian acoustic ECM hydrogel includes solubilized ECM at a concentration of about 20 mg/ml to about 70 mg/ml. In one non-limiting example, the mammalian acoustic ECM hydrogel includes solubilized ECM a concentration of about 40 mg/ml or about 66 mg/ml. In one non-limiting example, the mammalian acoustic ECM hydrogel includes solubilized ECM at a concentration of about 10 mg/ml to about 100 mg/ml. In one non-limiting example, the mammalian acoustic ECM hydrogel includes solubilized ECM at a concentration of about 50 mg/ml to about 150 mg/ml. In one non-limiting example, the mammalian acoustic ECM hydrogel includes solubilized ECM at a concentration of about 10 mg/ml to about 200 mg/ml. In one non-limiting example, the mammalian acoustic ECM hydrogel includes solubilized ECM at a concentration of about 10 mg/ml to about 500 mg/ml.

Exemplary concentrations include about 20 mg/ml, 40 mg/ml, 66 mg/ml, 70 mg/ml, and 150 mg/ml of solubilized ECM. In one non-limiting example, the mammalian acoustic ECM hydrogel includes about 20 mg/ml to about 70 mg/ml solubilized ECM. In one non-limiting example, the mammalian acoustic ECM hydrogel includes about 40 mg/ml or about 66 mg/ml of solubilized ECM.

In some embodiments, the mammalian acoustic ECM hydrogel includes solubilized ECM at a concentration of about 25 mg/ml to about 600 mg/ml. In further embodiments, the mammalian acoustic ECM hydrogel includes solubilized ECM at a concentration of about 20 mg/ml to about 600 mg/ml, about 25 mg/ml to about 300 mg/ml, about 25 mg/ml to about 200 mg/ml, and about 25 mg/ml to about 150 mg/ml. In more embodiments, the mammalian acoustic ECM hydrogel includes solubilized ECM at a concentration of about 50 mg/ml to 600 mg/ml. The mammalian acoustic ECM hydrogel also can include solubilized ECM at a concentration of about 50 mg/ml to about 300 mg/ml, about 50 mg/ml to about 200 mg/ml, about 50 mg/ml to about 150 mg/ml, about 50-100 mg/ml, or about 100-150 mg/ml. In some non-limiting examples, the mammalian acoustic ECM hydrogel includes solubilized ECM at a concentration of about 20-25, 25-30, 30-35, 35-40, 40-45, 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, and 195-200 mg/ml In some embodiments, to produce a mammalian acoustic ECM hydrogel, a comminuted ECM, such as a mammalian ECM, is diluted at a specific concentration in a liquid. The ECM may or may not be lyophilized prior to comminuting. The ECM can be comminuted, for example, by grinding, chopping or cutting the ECM. Comminuted ECM should have pieces in the range of about 10 μm to about 5000 μm, about 10 μm to about 4000 μm, about 10 μm to about 3000 μm, about 10 μm to about 2000 μm, about 10 μm to about 1000 μm, about 10 μm to about 500 μm, about 30 μm to about 300 μm, about 40 to about 400 μm, about 25 μm to about 500 μm, about 50 μm to about 500 μm, about 100 μm to about 300 μm, about 10 μm to about 50 μm, or about 10 μm to about 100 μm. In one embodiment, the ECM is provided in pieces having a range from about 10 μm to about 1000 μm. In another embodiment, the ECM is provided in pieces having a range from about 10 μm to about 2000 μm. In one non-limiting example, the pieces are in the range of about μm to about 300 μm.

The liquid can be a buffer at neutral pH, such as, for example, a pH of about 7.0 to about 7.6, such as about 7.1 to about 7.5, such as about 7.2 to about 7.4, such as about 7.0 to 7.2, such as about 7.0 to 7.4, such as about 7.1, 7.2, 7.3, 7.4, 7.5 or 7.6. The ECM can be diluted in an isotonic buffered saline solution, such as, but not limited to, phosphate buffered saline (PBS) or Tris buffered saline. In some embodiments, the buffered saline solution has an osmolarity of about 290 mOsm/L. The liquid can be water. In some embodiments, the isotonic buffer, including, without limitation, Phosphate Buffered Saline (PBS), can be used to bring the solution to a target pH, or to aid in maintaining the pH and ionic strength of the gel to target levels, such as physiological pH and ionic conditions. This forms a liquid ECM solution.

The methods used to produce the mammalian acoustic ECM hydrogel generally do not involve the use of an acid protease, including pepsin, trypsin, or hyaluronidase to solubilize the ECM. See PCT Application No. WO 2015/164728, incorporated herein by reference. Generally, in the present methods, the solubilized ECM in the liquid is not contacted with an acid protease. Thus, the mammalian acoustic ECM hydrogel does not comprise an exogenous protease or an inactivated exogenous protease. In some embodiments, the mammalian acoustic ECM hydrogel does not comprise exogenous pepsin, trypsin and/or hyaluronidase, or an inactivated form of exogenous pepsin, trypsin, or hyaluronidase.

The ECM in the liquid, such as the buffered saline solution, is treated with an ultrasound frequency to solubilize the ECM and produce the mammalian acoustic ECM hydrogel comprising solubilized ECM. In one embodiment, the ultrasound is at a frequency of about 20 kHz to about 100 kHz. The ECM in the liquid can be treated with ultrasound at a frequency of about 20 kHz to about 30 kHz, about 20 Hz to about 40 kHz, about 20 kHz to about 50 kHz, about 20 kHz to about 60 kHz, about 20 kHz to about 70 kHz, about 20 kHz to about 80 kHz, or about 20 kHz to about 90 kHz. The ECM in the liquid can be treated with ultrasound at a frequency of about 20 kHz, 30 kHz, 40 kHz, 50 kHz, 60 kHz, 70 kHz, 80 kHz, 90 kHz or 100 kHz. In one non-limiting example, the ECM in the liquid can be treated with ultrasound at a frequency of about 20 kHz.

The ECM in the liquid, such as the buffered saline solution, is treated with ultrasound for at least 20 seconds, such as at least 30 seconds. The ECM in the liquid, such as the buffered saline solution, is treated with ultrasound for at least 60 seconds. In some embodiments, the ECM in the liquid is treated with ultrasound for at least 60 seconds to about one hour. In further embodiments, the ECM in the liquid is treated with ultrasound for at least 60 seconds to about 30 minutes. In further embodiments, the ECM in the liquid is treated with ultrasound for at least 30 seconds to about 30 minutes. In more embodiments, the ECM in the liquid is treated with ultrasound for at least 60 seconds to about 15 minutes. In more embodiments, the ECM in the liquid is treated with ultrasound for at least 30 seconds to about 15 minutes. In some embodiments, the ECM in the liquid is treated with ultrasound for at least 60 seconds to about 10 minutes. In some embodiments, the ECM in the liquid is treated with ultrasound for at least 30 seconds to about 10 minutes. In some embodiments, the ECM in the liquid is treated with ultrasound for at least 60 seconds to about 5 minutes. In some embodiments, the ECM in the liquid is treated with ultrasound for at least 30 seconds to about 5 minutes. The ECM in the liquid can treated with ultrasound for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In some embodiments, the ECM in the liquid is treated with the ultrasound in pulses for a total time as listed herein. Thus, in some embodiments, the ECM in the liquid, such as the buffered saline solution, is treated with pulses, such as of at least about 30 seconds in length, such as about 30, about 40 or about 60 seconds in length. The ECM in the liquid such as the buffered saline solution, can be treated 1, 2, 3, 4, 5, 6, 7, 8, 9, 10 times, with the ultrasound, such that the total time of treatment is the 60 seconds to one hour, or any of the total times listed. The ECM in the liquid such as saline solution can be treated for 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 seconds. The ECM in the liquid such as saline solution can be treated for at least 30 seconds. Generally, if multiple treatments are used, they occur in a period of less than 1 hour. An exemplary method is pulses of 30 seconds of ultrasound, followed by no treatment for 30 to 45 seconds, followed by another treatment. This treatment is applied 2, 3, 4, 5, 6, 7, 8, 9 or 10 or more times. One exemplary non-limiting method is six pulses of 30 seconds of ultrasound, such as at about 20 kHz, followed by 45 seconds off, for six repetitions, totaling 3 minutes of treatment with ultrasound.

The ultrasound can have an amplitude of about 20 μm to about 320 μm. Generally, the amplitude is measure from the center of the probe used to produce the ultrasound. The amplitude of the probe's vibrating surface the distance between its position in the probe's fully extended and fully contracted states, measured in microns (μm). In some embodiments, the amplitude is about 30 μm to about 200 μm. In further embodiments, the amplitude is about 36 μm to about 180 μm. The amplitude can be about 30, 40, 50, 60, 70, 80, 90, 100, 110, 120, 130, 140, 150, 150, 160, 70, 180, 190, 200, 210, 220, 230, 240, 250, 260, 270, 280, 290 or 300 μm. In some embodiments, the amplitude can be about 30-40 μm, 40-50 μm, 50-60 μm, 60-70 μm, 70-80 μm, 80-90 μm, 90-100 μm, 100-110, 110-120 μm, 120-130 μm, 130-140 μm, 140-150 μm, 150-160 μm, 160-170 μm, 170-180 μm, 180-190 μm, 190-200 μm, 200-210 μm, 210-220 μm 220-230 μm, 230-240 μm, 240-250 μm, 250-260 μm, 260-270 μm, 270-280 μm, 280-290 μm or 290-300 μm. In one specific, non-limiting example, the ultrasound is at a frequency of about 20 kHz, and the amplitude is about 36 μm to about 180 μm. In a further non-limiting example, the ultrasound is at a frequency of about 20 kHz, and the amplitude is about 36 μm to about 180 μm, and the treatment is for a total of about 1, 2, 3, 4, or 5 minutes, such as about 3 minutes. The sonication can be for about 1, 2, 3, 4, 5, 6, 7, 8, 9, 10, 11, 12, 13, 14, 15, 16, 17, 18, 19 or 20 minutes. The sonication can be from about 30 seconds to about 5 minutes. The sonication can be for example, for between about 1 to about 5 minutes. The sonication can be for about 1 to about 10 minutes. The sonication can be, for example, for between 1 to about 20 minutes. In more embodiments, the sonication can be for less than about one hour, less than about 30 minutes, less than about 20 minutes, or less than about 10 minutes. In some embodiments, the sonication can be for at least 30 seconds. In other embodiments, the sonication can be for about 10 minutes to about 24 hours, for example, about 1, 2, 3, 4, 5, 6, 7, 8, 9, 10, 11, 12, 13, 14, 15, 16, 17, 18, 19, 20, 21, 22, 23, or 24 hours. In some embodiments, sonication can be for up to 48 hours.

In some embodiments, the ECM in the liquid is treated with the ultrasound at a temperature in a range of about 30° C. to about 43° C. In one embodiment, the ECM in the liquid is treated with the ultrasound at a temperature in the range of about 35° C. to about 40° C. In one embodiment, the ECM in the liquid is treated with ultrasound at a temperature in the range of about 36° C. to about 38° C. In another embodiment, the ECM in the liquid is treated with ultrasound at a temperature in the range of about 37° C. or greater, such as a temperature of about 37° C. to about 55° C., such as about 37° C. to about 50° C., such as about 37° C. to about 45° C., such as about 37° C. to about 40° C. The ECM in the liquid is treated with the ultrasound at a temperature of about 37, 38, 39, 40, 41, 42, 43, 44, 45, 46, 47, 48, 49, 50, 51, 52, 53, 54, or 55° C. In further embodiment, the ECM in the liquid is treated with the ultrasound at greater than about 38° C., such as about 38° C. to about 50° C., such as about 38° C. to about 45° C., such as about 38° C. to about 40° C.

Treatment with ultrasound produces the mammalian acoustic ECM hydrogel comprising solubilized ECM. The acoustic ECM hydrogel generally experiences a phase transition from sol to gel around 37° C. and is therefore transitions to a liquid phase at greater than 37° C., and to a gel phase at below 37° C. At 37° C. the mammalian acoustic ECM hydrogel is sufficiently viscous to resemble a gel, however as the temperature is increased above 37° C., the gel transitions to a sol. The mammalian acoustic ECM hydrogel forms a gel (sol to gel transition) upon a decrease in temperature below 37° C. Thus, in some embodiments, following sonication, the mammalian acoustic ECM hydrogel is cooled to a temperature of less than 37° C., such as about 4° C. to about 36° C. The acoustic ECM hydrogel can be cooled to room temperature, which is generally about 25° C. In some embodiments, the acoustic ECM hydrogel is cooled to about 15° C. to about 25° C. The acoustic ECM hydrogel can be cooled to about 23° C. to about 27° C. The acoustic ECM hydrogel can be cooled to about 4, 5, 6, 7, 8, 9, 10, 11, 12, 13, 14, 15, 16, 17, 18, 19, 20, 21, 22, 23, 24, 25, 26, 27, 28 29 or 30° C.

In some embodiments, the mammalian acoustic ECM hydrogel is thermoreversible, wherein the hydrogel is in a solid (gel) phase at temperatures below about 37° C. and is in a liquid (sol) phase at temperatures of greater about 37° C. The acoustic hydrogel can be produced using any of the methods disclosed herein.

In some embodiments, the storage modulus (G') is greater than loss modulus (G") by about one order of magnitude. In further embodiments, wherein the viscosity of the mammalian acoustic ECM hydrogel decreases with increased stress at a temperature of about 15 to about 37° C., such as at about 15, 15, 16, 17, 18, 20, 21, 22, 23, 24, 25, 26, 27, 28, 29, 30, 31, 32, 33, 34, 35, and/or 36° C. In further embodiments, the viscosity of the mammalian acoustic ECM hydrogel decreases with increased stress at room temperature, and/or at about 23° C. to about 27° C. and/or about 15° C. to about 25° C. In one embodiment, the gel to sol transition of the acoustic ECM hydrogel is at about 37° C., such that the hydrogel can be used as in an anal fistula because it is sufficiently viscous at body temperature. As discussed below, a composition can be produced that includes the mammalian acoustic ECM hydrogel and trehalose.

In some embodiments, the composition has a storage modulus (G') to loss modulus (G") ratio in the range of about 6:1 to about 12:1 at 37° C. Thus, in some embodiments, the composition has a storage modulus (G') to loss modulus (G") ratio of 6:1, 7:1, 8:1, 9:1, 10:1, 11:1, or 12:1 at 37° C. In more embodiments, the composition has a storage modulus (G') to loss modulus (G") ratio in the range of about 7:1 to about 11:1 at 37° C., such as about 8:1 to about 10:1 at 37° C.

In more embodiments, the composition has a storage modulus (G') of about 5 to about 15,000 Pa. In more embodiments, the composition can have a G' of about 5 to about 10,000 Pa, about 5 to about 5,000 Pa, about 5 to about 500 Pa, or about 5 to about 50 Pa. In further embodiments, the composition can have a G' of about 10 to about 15,000 Pa, about 100 to about 15,000 Pa, about 1,000 to about 15,000 Pa, about 2,000 to about 15,000 Pa, about 3,000 to about 15,000 Pa, about 4,000 to about 15,000 Pa, about 5,000 to about 15,000 Pa, about 6,000 to about 15,000 Pa, about 7,000 to about 15,000 Pa, about 8,000 to about 15,000 Pa, about 9,000 to about 15,000 Pa, about 10,000 to about to about 15,000 Pa, about 11,000 to about 15,000 Pa, about 12,000 to about 15,000 Pa, about 13,000 to about 15,000 Pa, or about 14,000 to about 15,000 Pa.

In some embodiments, the composition has a viscosity of between about 0.1 and 1 $s^{-1}$. The composition can have a viscosity of about 0.1 to about 0.5 $s^{-1}$ or about 0.5 to about 1 $s^{-1}$. The composition can have a viscosity of about 0.2 to about 0.9 $s^{-1}$, or about 0.3 to about 0.8 $s^{-1}$, or about 0.4 to about 0.7 $s^{-1}$, or about 0.5 to about 0.6 $s^{-1}$. In further embodiments, the composition has a viscosity of about 0.1, 0.2, 0.3, 0.4, 0.5, 0.6, 0.7, 0.8, 0.9 or 1.0 $s^{-1}$.

In some embodiments, a composition is produced that includes the mammalian acoustic ECM hydrogel and trehalose. In more embodiments, a composition is used includes about 0.1 mg/ml to about 700 mg/ml of trehalose. In some embodiments, the composition includes about 1 mg/ml trehalose to about 700 mg/ml trehalose. In further embodiments, the composition includes 50 mg/ml to about 500 mg/ml trehalose. In other embodiments, the composition includes about 10 mg/ml trehalose to about 600 mg/ml, about 10 mg/ml to about 500 mg/ml, about 10 mg/ml to about 400 mg/ml, about 10 mg/ml to about 300 mg/ml, about 10 mg/ml to about 200 mg/ml, or about 10 mg/ml to about 100 mg/ml trehalose. In further embodiments, the composition can include about 0.1 to about 100 mg/ml trehalose, about 0.1 to about 10 mg/ml trehalose, or about 0.1 to about 1 mg/ml trehalose. In more embodiments, the composition can include about 50 mg/ml to about 400 mg/ml trehalose, about 50 mg/ml to about 300 mg/ml trehalose, about 50 mg/ml to about 200 mg/ml trehalose, or about 50 ml/ml to about 100 mg/ml trehalose. In some embodiments, the composition includes about 20 mg/ml to about 70 mg/ml trehalose. In some embodiments, the composition includes about 10 mg/ml to about 100 mg/ml trehalose. In some embodiments, the composition includes 15-30 mg/ml trehalose. In some embodiments, the composition includes 60-70 mg/ml trehalose. In some embodiments, the composition includes 20 mg/ml trehalose. In some embodiments, the composition includes 66 mg/ml trehalose. In other embodiments, the composition can include about 1, 2, 3, 4, 5, 6, 7, 8, 9, 10, 20, 30, 40, 50, 60, 66, 70, 80, 90, 100, 200, 300, 400, 500, or 600 mg/ml of trehalose. In other embodiments, the composition includes about 100 mg/ml to about 700 mg/ml trehalose, such as about 100, 150, 20, 250, 300, 350, 400, 450, 500, 550, or 600 mg·ml trehalose. In more embodiments, the composition can include about 0.1, 0.2, 0.3, 0.4, 0.5, 0.6, 0.7, 0.8, 0.9 or 1 mg/ml trehalose.

In more embodiments, the composition includes the mammalian acoustic ECM hydrogel comprising solubilized ECM, additional comminuted mammalian ECM, and optionally trehalose. Comminuted ECM is not treated with ultrasound, and is not solubilized into the hydrogel. The comminuted ECM is a distinct additive to composition that also includes the mammalian ECM hydrogel. The composition can include about 1 to about 30% comminuted ECM, weight per volume (w/v), that is not solubilized in the acoustic ECM hydrogel. Without being bound by theory, comminuted ECM generally has intact collagen particles, whereas an acoustic ECM hydrogel has collagen that has been disrupted by ultrasound resulting in an increase in soluble collagen content (Hussey et al., Ultrasonic cavitation to prepare ECM hydrogels Acta Biomater. 2020 May; 108: 77-86, incorporated herein by reference in its entirety, see, for example, FIG. 2). As such, an acoustic ECM hydrogel composition containing additional comminuted mammalian ECM includes both intact collagen and disrupted collagen.

The composition can include about 5% to about 30% w/v, about 10% to about 30%, about 15% to about 30%, about 20% to about 30%, about 25% to about 30%, about 1% to about 20%, about 5% to about 20%, about 10% to about 20%, about 15% to about 20%, about 10% to about 20%, or about 15% to about 20% comminuted ECM (w/v). The composition can include about 1, 2, 3, 4, 5, 6, 7, 8, 9, 10, 15, 20, 25, or 30% comminuted ECM (w/v). The composition can include no more than 1, 2, 3, 4, 5, 6, 7, 8, 9, 10, 15, 20, 25, or 30% comminuted ECM (w/v). The composition can include at least about 1, 2, 3, 4, 5, 6, 7, 8, 9, 10, 15, 20, 25, or 30% comminuted ECM (w/v).

Comminuted ECM can be from the same species as the mammalian acoustic ECM hydrogel. In one specific non-limiting example, both the mammalian acoustic ECM hydrogel and the comminuted ECM are porcine. In other non-limiting examples, both the mammalian acoustic ECM hydrogel and the comminuted ECM are human.

The comminuted ECM can be from the same or different tissue as the mammalian acoustic ECM hydrogel. In one embodiment, the mammalian acoustic ECM hydrogel and the comminuted ECM are from the same tissue. In one embodiment, the mammalian acoustic ECM hydrogel and the comminuted ECM are dermal ECM. In one embodiment, the mammalian acoustic ECM hydrogel and the comminuted ECM are porcine dermal ECM.

In a specific non-limiting example, the composition includes: i) a mammalian acoustic extracellular matrix (ECM) hydrogel, wherein: a) the mammalian acoustic ECM hydrogel is thermoreversible, wherein the mammalian acoustic ECM hydrogel is in a gel phase at temperatures below about 37° C. and transitions to a liquid phase at temperatures above about 37° C., and b) the mammalian acoustic ECM hydrogel comprises solubilized ECM at a concentration of about 0.1 mg/ml to about 1,000 mg/ml. The composition also includes: i) 0.1 mg/ml to about 700 mg/ml trehalose. The composition also includes ii) about 1 to about 30% (weight per volume) of comminuted ECM that is not solubilized in the hydrogel. In some embodiments, the composition has a storage modulus (G') to loss modulus (G") ratio of about 6:1 to about 12:1 at 37° C.

In a specific non-limiting example, the composition includes: i) a mammalian acoustic extracellular matrix (ECM) hydrogel, wherein: a) the mammalian acoustic ECM hydrogel is thermoreversible, wherein the mammalian acoustic ECM hydrogel is in a gel phase at temperatures below about 37° C. and transitions to a liquid phase at temperatures above about 37° C., b) the mammalian acoustic ECM hydrogel comprises solubilized ECM at a concentration of about 0.1 mg/ml to about 1,000 mg/ml, and c) the composition has a storage modulus (G') to loss modulus (G") ratio of about 6:1 to about 12:1 at 37° C. The composition also includes: ii) 0.1 mg/ml to about 700 mg/ml trehalose. The composition also includes iii) about 1 to about 30% (weight per volume) of comminuted ECM that is not solubilized in the hydrogel. In several nonlimiting examples, the mammalian acoustic ECM hydrogel comprises urinary bladder ECM, small intestinal submucosal ECM, esophageal ECM, trachea ECM, liver ECM, or dermal ECM. In other non-limiting examples, the ECM is porcine ECM. In other non-limiting examples, the ECM is dermal ECM. In other non-limiting examples, the ECM is porcine dermal ECM. In further non-limiting examples, the mammalian acoustic ECM hydrogel does not comprise an exogenous protease or an inactivated exogenous protease, such as exogenous pepsin, trypsin or hyaluronidase or an inactivated form of exogenous pepsin, trypsin, or hyaluronidase. In more non-limiting examples, the composition comprises about 50 to about 500 mg/ml trehalose. In yet other non-limiting examples, the composition has a storage modulus (G') of about 5 to about 15,000 Pa. In further non-limiting examples, the composition has a viscosity of between about 0.1 and 1 $s^{-1}$ and a storage modulus of 5-15,000 Pa at a temperature of about 25° C. In other non-limiting examples, the mammalian solubilized ECM concentration in the mammalian acoustic ECM hydrogel is about 20 mg/ml to about 70 mg/ml, such as about 40 to about 66 mg/ml. Other aspects of the disclosed compositions are provided above.

The composition can be sterilized prior to application to a subject. The composition can be sterilized using any methods known to those of skill in the art, including filtration and radiation. In some embodiments, the composition is sterilized with ionizing radiation, such as e-beam or gamma radiation. The composition can be sterilized using gamma radiation, for example, the composition is sterilized using 10 to 50 kGy irradiation, such as 15 to 45 kGy irradiation, 20 to 40 kGy irradiation, or 10 to 30 kGy of irradiation. In some non-limiting examples, the composition is sterilized using 10, 15, 20, 25, 30, 35, 40, 45 or 50 kGy irradiation. Generally, the composition is sterilized for a sufficient time to achieve an absence of detectable viable pathogens, such as, but not limited to, viruses and bacteria.

Antibiotics or antimicrobial agents may be added to the composition to reduce the potential for infection at the treatment site. A variety of antibiotics are known, including those that target the bacterial cell wall (for example, penicillins and cephalosporins) or the cell membrane (for example, polymixins), or interfere with essential bacterial enzymes (for example, quinolones and sulfonamides). Antibiotics include, but are not limited to, clindamycin, erythromycin, tetracycline, minocycline, doxycycline, penicillin, ampicillin, carbenicillin, methicillin, cephalosporins, vancomycin, and bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, inezolid, pharmaceutically acceptable salts thereof, and prodrugs thereof. Antibacterial agents also include cyclic lipopeptides (such as daptomycin), glycylcyclines (such as tigecycline), and oxazolidinones (such as linezolid). The antibiotic can be a narrow-spectrum or broad-spectrum antibiotic. The antibiotic can target gram negative or gram positive bacteria. Topical antibiotic can be included, such as a macrolide antibiotic (such as erythromycin), a sulfa antibiotic (such as sulfacetamide), a cyclic peptide (such as bacitracin a polymyxin) a psuedomonic acid (such as mupirocin), an aminoglycoside (such as neomycin), or a quinolone (such as ciprofloxacin or ofloxacin), a nitroimidazole (such as metronidazloe), or a combination of drugs (such as bacitracine/polymyxin or neomycin/polymyxin B/bacitracin).

Additionally, local anesthetics may be added to the composition to minimize discomfort, such a lidocaine. Any appropriate additive may be utilized as long as it is compatible with the composition and the particular patient and disease state being treated.

In some embodiments, the composition, such as the sterilized composition, is injectable through a 5 Fr/16 G catheter. in one embodiment, the composition is injectable through a 5 Fr/16 G catheter at room temperature, or at both room temperature and about 37° C.

Any useful agent can be mixed into, co-delivered, co-applied or otherwise combined with any composition as described herein. For example, and without limitation, useful agents include interferons, interleukins, chemokines, cytokines, hormones, coagulants, chemotherapeutics and antibiotics.

Enzymatic ECM Hydrogels and Compositions for Use

Compositions are disclosed herein that can be administered locally to a fistula, for example, an anal fistula, and thus used for treatment of the fistula, e.g., to close the fistula. The compositions include a mammalian enzymatic extracellular matrix (ECM) hydrogel that is thermoreversible, and is in a gel phase at temperatures from 37° C. and up and transitions to a liquid phase at temperatures below about 37° C. Enzymatically produced ECM hydrogels are discussed, for example, in U.S. Pat. No. 8,361,503, which is incorporated by reference herein in its entirety for all purposes. Preparation of terminally sterilized enzymatically produced ECM hydrogels are discussed, for example, in U.S. Pat. No. 10,213,526, which is incorporated by reference herein in its entirety for all purposes.

"Enzymatic ECM hydrogels" refers to hydrogels composed of extracellular matrix where the ECM is enzymatically digested. For example, the ECM may be digested by a protease, for example, an acid protease such as trypsin or pepsin.

Enzymatic ECM hydrogels can be made from any mammalian ECM source tissue or organ, including without limitation, urinary bladder, intestine (such as small intestine or large intestine), heart, kidney, uterus, brain, blood vessel, lung, bone, muscle, pancreas, stomach, spleen, adipose tissue, muscle tissue, liver, esophagus, placenta, and dermis. The source of ECM can be, for example, porcine, bovine, human or ovine. In specific, non-limiting example, the ECM is porcine ECM. In other non-limiting examples, the ECM is urinary bladder ECM, small intestinal submucosal ECM, esophageal EMC, tracheal ECM, liver ECM, or dermal ECM. In one embodiment, the ECM is urinary bladder ECM. In another embodiment, the ECM is dermal ECM. In yet another embodiment, the ECM is small intestinal submucosal ECM.

Enzymatic ECM hydrogels are produced through enzymatic digestion of extracellular matrix under certain conditions. For example, a method of preparing an enzymatic extracellular matrix-derived gel is provided. In one embodiment, the method comprises: (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution, and (iv) gelling the neutralized digest solution at a temperature greater than approximately 25° C.

In one non-limiting embodiment, the ECM is lyophilized and comminuted and then solubilized with an acid protease. The acid protease may be, without limitation, pepsin or trypsin, and in one embodiment is pepsin. The ECM typically is solubilized at an acid pH suitable or optimal for the protease, such as greater than about pH 2, or between pH and 4, for example in a 0.01M HCl solution. The solution typically is solubilized for 12-48 hours, depending upon the tissue type, with mixing (stirring, agitation, admixing, blending, rotating, tilting, etc.).

Once the ECM is solubilized (typically substantially completely) the pH is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution can be gelled at temperatures approaching 37° C., typically at any temperature over 25° C., though gelation proceeds much more rapidly at temperatures over 30° C., and as the temperature approaches physiological temperature (i.e., 37° C.). The method typically does not include a dialysis step prior to gelation, yielding a more-complete ECM-like matrix that typically gels at 37° C. more slowly than comparable collagen or dialyzed ECM preparations.

In one embodiment, the enzymatic ECM hydrogel is terminally sterilized. "Terminal sterilization" of an enzymatic ECM hydrogel refers to the essentially or practically complete sterilization of the composition. Terminal sterilization, does not include disinfection, e.g., with peracetic acid during preparation of an ECM product as part of or ancillary to decellularization of ECM.

In one embodiment, a terminally sterilized enzymatic ECM hydrogel is prepared by (i) comminuting an extracellular matrix, (ii) solubilizing intact, non-dialyzed or non-cross-linked extracellular matrix by digestion with an acid protease in an acidic solution to produce a digest solution, (iii) drying the digest solution to produce a dried digest, (iv) terminally sterilizing the dried digest to produce a sterilized, dried digest, (iv) hydrating the sterilized dried digest to produce a sterilized digest solution, and (v) raising the pH of the sterilized digest solution to a pH between 7.2 and 7.8 to produce a neutralized, sterilized digest solution. The neutralized, sterilized digest solution may also be referred to as a "pre-gel." The neutralized digest solution or pre-gel can then be gelled by raised the temperature of the neutralized digest solution to a temperature greater than approximately 25° C.

Terminal sterilization of the dried digest may be achieved, for example, by electron beam or gamma radiation, exposure to ethylene oxide gas or to supercritical carbon dioxide.

Drying of the digest solution may be achieved, for example, by air drying or lyophilization or heating. By "dry," "drying" or "dried," it is meant dried or lyophilized to a point that essentially all water is removed from a composition, recognizing that in practice, one may not literally remove all water molecules from any composition. Thus "dry" or "dried" refers to a water content of, for example and without limitation, less than 5.0, 1.0, 0.5, 0.1, 0.01, 0.001 or 0.0001% by weight of the composition (% wt.). Material can be dried by any process, such as, for example and without limitation, by simple evaporation at any non-damaging temperature, such as at room temperature, or by lyophilization (freeze drying).

Hydrating the sterilized dried digest may be achieved, for example, by solubilization in sterile water or in an aqueous solution such as a TRIS buffer or PBS, or a salt solution such as a sodium chloride solution, such as (0.9%) saline to produce a sterilized digest solution.

Neutralizing the hydrated digest solution may be achieved, for example, by mixing the solution with an isotonic buffer or a base, such as, without limitation NaOH. Accordingly, in one embodiment, the invention provides a gellable extracellular matrix (ECM) composition comprising a decellularized, enzymatically digested, dried, terminally sterilized, intact extracellular matrix, wherein said composition is capable of forming a gel upon hydration, neutralization to pH 7.2-7.8, and warming to a temperature greater than 25° C. for use in the repair of a fistula. For example, the composition is used to fill a fistula tract, for example, in a human. In one embodiment, the composition comprises an inactivated protease, for example, trypsin or pepsin. For example, the fistula is an anal fistula. In one embodiment, the composition forms a gel when warmed to 37° C.

Accordingly, in one embodiment, the invention provides a terminally sterilized extracellular matrix (ECM) digest solution comprising decellularized, enzymatically digested, terminally sterilized, intact extracellular matrix, wherein said composition is capable of forming a gel upon neutralization to pH 7.2-7.8, and warming to a temperature greater than 25° C. for use in the repair of a fistula. For example, the composition is used to fill a fistula tract, for example, in a human. In one embodiment, the composition comprises an inactivated protease, for example, trypsin or pepsin. For example, the fistula is an anal fistula. In one embodiment, the composition comprises an inactivated protease, for example, trypsin or pepsin. In one embodiment, the composition forms a gel when warmed to 37° C. In one embodiment, the solution is an acidic solution.

Accordingly, in one embodiment, the invention provides a terminally sterilized extracellular matrix (ECM) digest solution comprising a hydrated, decellularized, enzymatically digested, terminally sterilized, intact extracellular matrix, wherein said digest solution has a pH 7.2-7.8 and forms a gel when warmed to a temperature greater than 25° C. for use in the repair of a fistula. For example, the composition is used to fill a fistula tract, for example, in a human. In one embodiment, the composition comprises an inactivated protease, for example, trypsin or pepsin. For example, the fistula is an anal fistula. In one embodiment, the composition comprises an inactivated protease, for example, trypsin or pepsin. In one embodiment, the composition forms a gel when warmed to 37° C.

Methods of Use

The presently disclosed compositions can be used for treating a fistula in a subject. For example, in one non-limiting embodiment, the fistula is an anal fistula. Most anal fistulas are primary, i.e. a developing consequence of non-specific infections from the anal glands, after the formation of perianal abscesses.

Anal fistula is a chronic infectious duct communicated with the perianal skin and rectum/anal canal, and consists of an inner opening, a fistula and an outer opening. Anal fistula is clinically manifested by recurrent perianal infection, ulceration and pus discharge, and perianal cancer can occur in patients who are not healed for a long time. Traditional treatment methods include fistula excision, fistula incision, thread hanging therapy, fistula open drainage, and trans-anorectal mucosa flap internal orifice repair.

Examples described herein relate to the repair (e.g., closing) of lumens in a patient, such as anal fistulas and other types of fistulas. In particular, examples described herein include the use of a composition, as disclosed herein, formulated for delivery to a lumen such as a fistula. The subject can be any subject, including a veterinary or a human subject. A human subject can be of any age, including adults and children.

In some embodiments, the compositions disclosed herein promotes tissue growth across a fistula in order to provide permanent closure. Thus, in some embodiments, the disclosed compositions fill the lumen of any fistula.

A fistula that takes a straight-line path from the primary opening to the secondary opening is known as simple fistula. A fistula that contains multiple tracts ramifying from the primary opening and has multiple secondary openings is known as a complex fistula. The disclosed methods can be used to treat both a simple fistula and a complex fistula.

In some embodiments, a subject is selected for treatment that has a fistula. The fistula can be an enterocutaneous fistula (intestine to skin), colocutaneous (large intestine/colon to skin), enteroenteral fistula (intestine to intestine), vesicointestinal fistula (bladder to bowel), vesicocoli fistula (bladder to colon), vesicorectal (bladder to rectum), rectovaginal fistula (vagina to rectum), vesicovaginal (vagina to bladder), rectouterine (uterus to bowel/rectum), vesicouterine (uterus to bladder), uretovaginal (ureter to vagina), metroperitoneal (uterus to peritoneal cavity), or a enterovaginal (bowel to vagina). In some examples, the disclosed compositions can be used to treat recto-vaginal fistulas. The fistula can be an anorectal, recto-vaginal, enterocutaneous, tracheo-esophageal, biliary-enteric, vesico-vaginal, vesico-intestinal, entero-enteral, pancreatic, cryptoglandular, Crohn's, dural-sinus, colo-vesical, colo-enteric, colo-vaginal, colo-enteric, recto-urethral, or pharyngo-cutaneous fistula.

The fistula can be an anal fistula. The goal of a surgical repair of an anal fistula may be to close the fistula with as little impact as possible on the sphincter muscles. In some settings, a composition as described herein can be delivered locally into the fistula, such as by injection into the lumen. In some embodiments, tissue growth is promoted across the lumen of the anal fistula. The anal fistula can be simple or complex.

The anatomic path that an anorectal fistula takes is classified according to its relationship to the anal sphincter muscles. The anal sphincter includes two concentric bands of muscle: the inner, or internal, sphincter and the outer, or external, anal sphincter. A fistula which passes between the two concentric anal sphincters is known as an inter-sphincteric fistula. A fistula which passes through both internal and external sphincters is known as a trans-sphincteric fistula, and a fistula which passes above both sphincters is called a supra-sphincteric fistula. A fistula that results from Crohn's disease usually ignores these anatomic paths, and is known as an extra-sphincteric fistula. In one complex type of fistula, the infection starts in the anal gland (the primary opening) and two fistulae pass circumferentially around the anal canal, forming a characteristic horseshoe configuration. The disclosed methods can be used to treat all of these types of fistulae.

Methods have evolved to inject sclerosant or fibrin glue into the tract of the fistula. Any of these methods, see for example, U.S. Pat. No. 5,752,974 (incorporated herein by reference) can be used with the compositions that are disclosed herein. A disclosed composition can be applied by injection, using a syringe, using an endoscope, or a catheter. In some embodiments, the disclosed composition is applied to fill the fistula. Exemplary amounts are 1 ml to 5 ml, although one of skill in the art, such as a clinician, can readily determine an appropriate amount based on clinical parameters, such as the diameter and length of the fistula, and/or the method of administration, such as via a catheter or endoscope.

In some embodiments, preliminary endoscopic visualization (fistuloscopy) and "cleaning" of the fistula tract is performed. This procedure may be performed by a very thin flexible endoscope, which is inserted into the secondary opening of the fistula tract, and advanced under direct vision through the fistula tract and out the primary opening. By performing preliminary fistuloscopy of the fistula tracts, the primary opening is accurately identified, and the tracts are "cleaned out" by means of an irrigating fluid. Any inflammatory or necrotic tissue within the tract is therefore removed. Following this treatment, an application device, such as a syringe, catheter or endoscope, is inserted that allows application of a disclosed composition. In some embodiments, the disclosed composition is applied to fill the fistula. For example, the hydrogel composition is injected into the fistula to fill it from end to end. Because the hydrogel is in the gel state at body temperature, it remains in the fistula tract and is absorbed by the body as the fistula heals. One of skill in the art, such as a physician, can readily determine methods for administration of the disclosed composition, and evaluation of the outcome of treatment.

In a specific non-limiting example, a subject can receive an antibiotic prior to the use of the disclosed compositions. Suitable antibiotics include, but are not limited to, cefuroxime and/or ornidazole. In one embodiment, the subject is anesthetized. Suitable procedures for anesthesia include, but are not limited to, spinal anesthesia. Under spinal anesthesia in the prone jackknife position, the fistula is probed to determine the external and internal fistula tract openings. An anal retractor can be used.

In some embodiments, the tract is curetted with polyester tape (such as of a white braided fiber, ⅛" wide). The tract can be cleaned, such as using a blunt curette or gauze strip. In some embodiments, the tract is debrided, such as to remove granulation tissue, and then cleaned with a solution, such as phosphate buffered saline. The composition is instilled into the fistula tract by way of an external opening, so the tip of the injection device is seen emerging from the internal opening into the anal canal. In some embodiments a tube or other injection device is introduced to the bottom of the fistula-in-ano and then continuously withdrawn during the injection to completely fill the fistula with the composition. After the composition is introduced, any anal retractor can be removed. Postoperative analgesics can be used. In some embodiments, perioperative oral intake is restricted, such as for about 24 hours. Patients can be placed on a liquid diet for about one to about 2 days following the procedure, and then gradually advanced to their regular diet. Physical examinations can be conducted.

While examples herein are discussed in the context of an anorectal fistula, it should be understood that the following exemplary devices and techniques may be readily applied to various other types of fistulas, such as, but not limited to, enterocutaneous fistula (intestine to skin), colocutaneous fistula (large intestine/colon to skin), enteroenteral fistula (intestine to intestine), vesiconintestinal fistula (bladder to bowel), vesicocoli fistula (bladder to colon), vesicorectal fistula (bladder to rectum), rectovaginal fistula (vagina to rectum), vesicovaginal fistula (vagina to bladder), rectouterine fistula (uterus to bowel/rectum), vesicouterine fistula (uterus to bladder), uretovaginal fistula (ureter to vagina), metroperitoneal fistula (uterus to peritoneal cavity), or enterovaginal fistula (bowel to vagina), and a trachea-esophageal fistula.

In some embodiments, the use of the disclosed compositions results in healing of the anal fistula. Thus, the fistula can be sealed immediately following application. In other embodiments, the use of the disclosed composition promotes tissue growth that seals the fistula, such as in days, weeks or a month following the use of the composition. In yet other embodiments, following use of the disclosed composition, tissue growth can be induced within 1, 2, 3, 4, 5, 6, 7, 8, 9, 10, 11, 12, 13, or 14 days following the use of the disclosed composition. Tissue growth can also be induced within 1, 2, 3 or 4 weeks following the use if the disclosed composition. In some embodiments, the composition is absorbed into the body and displaced by tissue growth such that the fistula tract is replaced with tissue and the composition is no longer present after several days or weeks.

In further embodiments, the use of the disclosed composition modulates macrophages toward a pro-remodeling phenotype (Fizz-1+). Thus, in some embodiments, the use of the disclosed composition increases the number of Fizz-1+ macrophages at the site of the anal fistula.

EXAMPLES

A space-filling, pro-remodeling, colloidal hydrogel derived from decellularized extracellular matrix (ECM) is disclosed that can be used to treat fistulas, such as anorectal fistulas or any other fistula disclosed herein. ECM, such as from porcine dermis (dECM) was exposed to ultrasonication in the presence of a physiologic buffer and supplemented with additional dECM powder ("colloid") and trehalose, and cooled to form an injectable hydrogel. In vitro results demonstrate that this type of ECM hydrogel is a stiff biomaterial capable of filling fistula tracts of complex architecture at body temperature, can modulate macrophages toward a pro-remodeling phenotype (Fizz+), and has hemostatic properties. The hydrogel maintained its rigidity in ex vivo tracts and did not degrade or leak out of the tract at body temperature.

In a post-mortem, ex-vivo porcine fistula model, the biomaterial was capable of filling tracts without leakage at body temperature. The space-filling, anti-inflammatory, and hemostatic capabilities of a colloidal ECM hydrogel make it effective for the treatment of simple and complex anorectal fistulas. The ease of injection, sterility, and stability of the biomaterial, at both room and body temperature, allow this biomaterial to be used "off-the-shelf" by physicians in both surgical and out-patient settings. ECM colloidal hydrogels can improve healing, mitigate operative bleeding, and reduce complications and recurrence in the management of anorectal fistulas.

Example 1

Hydrogel Stability

It has been previously shown that well-accepted terminal sterilization methods (i.e., gamma irradiation, electron beam irradiation, ethylene oxide (EtO) exposure) inhibit formation of an ECM hydrogel prepared using the pepsin digestion method (White et al., *Front. Bioeng. Biotechnol. Conference Abstract:* 10*th World Biomaterials Congress*. doi: 10.3389/conf.FBIOE.2016.01.00032 and White et al., *Journal of Immunology and Regenerative Medicine.* 2018; 2:11-20). Therefore, studies were conducted to determine if terminal sterilization inhibits gelation of an ECM hydrogel prepared using the ultrasonic method. This example shows that addition of trehalose to the acoustic hydrogel material prior to sterilization is conducive to retaining the properties of the hydrogel after sterilization.

As shown in FIG. 1 (left panel), sterilization of the acoustic gel using 35 kGy E-beam, caused the sample to form a series of aggregates rather than a uniform consistency. However, addition of Trehalose at either 20 or 40 mg/ml prevented the acoustic ECM hydrogel from forming aggregates after sterilization with 35 kGy E-beam FIG. 1 (right panels); rather the consistency was uniform.

Figure 2:
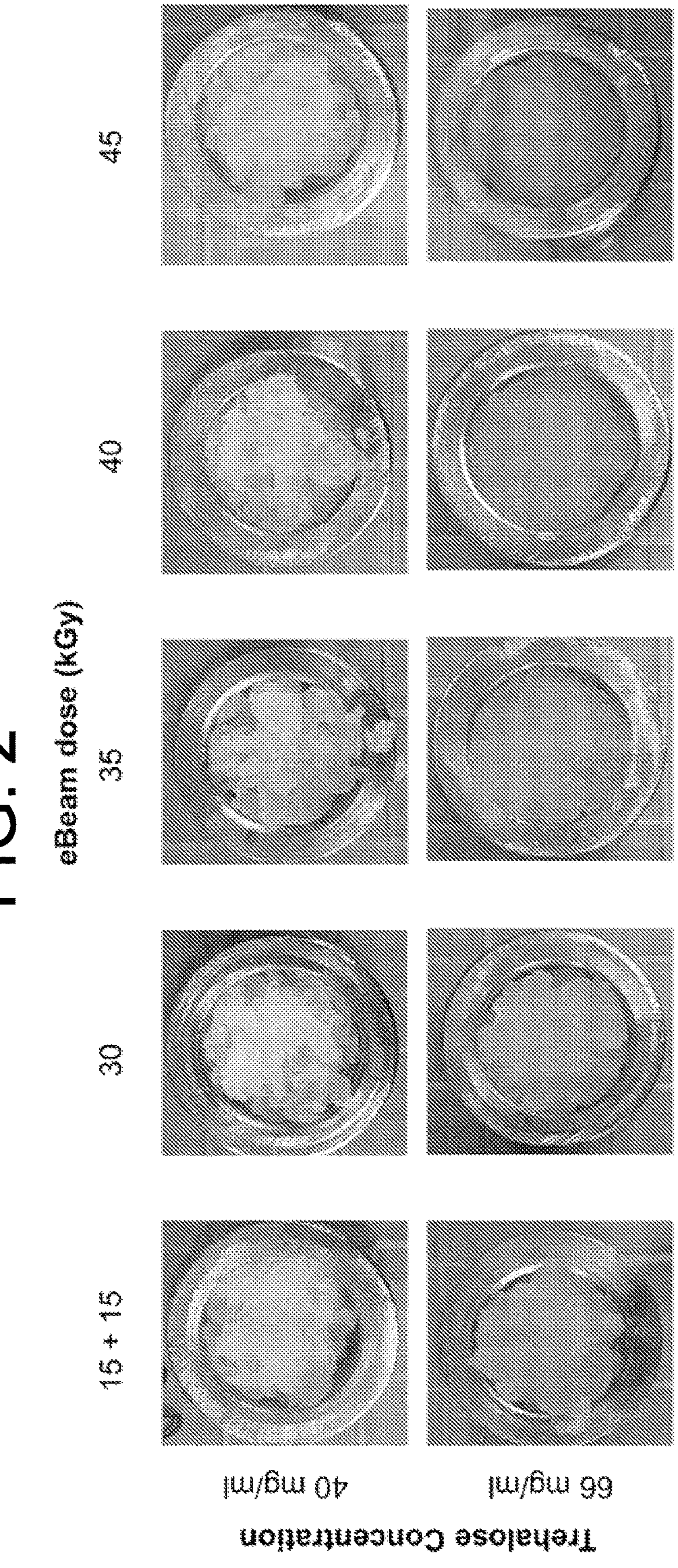
FIG. 2: Macroscopic Gelation tests. 5% colloid dECM hydrogels containing 40 or 66 mg/ml trehalose were subjected to E-beam sterilization at the indicated dosages. After sterilization, the samples were chilled to 4° C. and injected into ring molds. Macroscopic evaluation showed that when injected cold, the 5% colloid dECM hydrogel containing 40 mg/ml trehalose formed more aggregates than the dECM 5% colloid hydrogel containing 60 mg/ml trehalose at all E-beam doses tested.

Next, it was determined if trehalose could prevent the formation of aggregates in a colloidal acoustic hydrogel. After solubilization of 100 mg/ml dermal ECM using the ultrasonic cavitation method, additional comminuted dermal ECM was then added to the suspension as a thickening agent to produce colloidal ECM hydrogels ranging from 0.1 to 20% colloid (w/v). As shown in FIG. 2, 5% (w/v) colloid acoustic gels prepared with either 40 or 66 mg/ml Trehalose were sterilized using increasing dosage of E-beam irradiation. After sterilization, the samples were chilled to 4° C. and injected into ring molds. Macroscopic evaluation showed that when injected into the ring mold at 4° C., the 5% colloid hydrogels containing 40 mg/ml trehalose formed more aggregates than the dECM colloid hydrogel containing 66 mg/ml trehalose at all E-beam doses tested.

Figure 3:
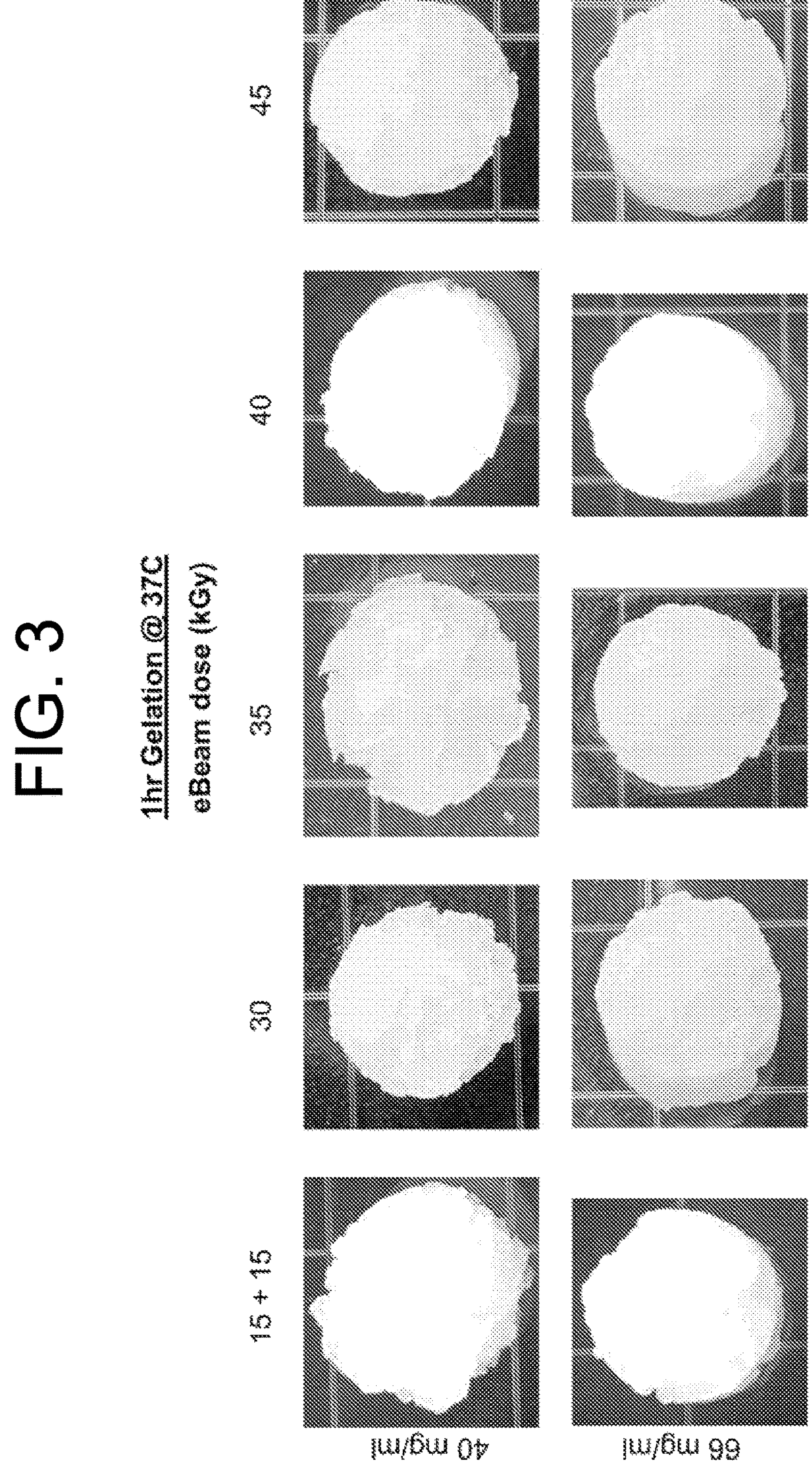
FIG. 3: Macroscopic Gelation tests at 37° C. 5% colloid hydrogels containing 40 or 66 mg/ml trehalose were subjected to E-beam sterilization at the indicated dosages. After sterilization, the samples were chilled to 4° C. and injected into ring molds. The samples were then placed in a 37° C. incubator for 1 hr. Macroscopic evaluation showed that dECM colloid hydrogels containing trehalose as a radioprotectant, and subjected to E-beam sterilization, maintain their shape at 37° at both concentrations of trehalose.

In a separate set of experiments, the samples were chilled to 4° C.; injected into ring molds; and then placed in a 37° C. incubator for 1 hr and then the ring mold carefully removed to determine if the colloid gels could hold their shape after E-beam sterilization (FIG. 3).

Figure 4:
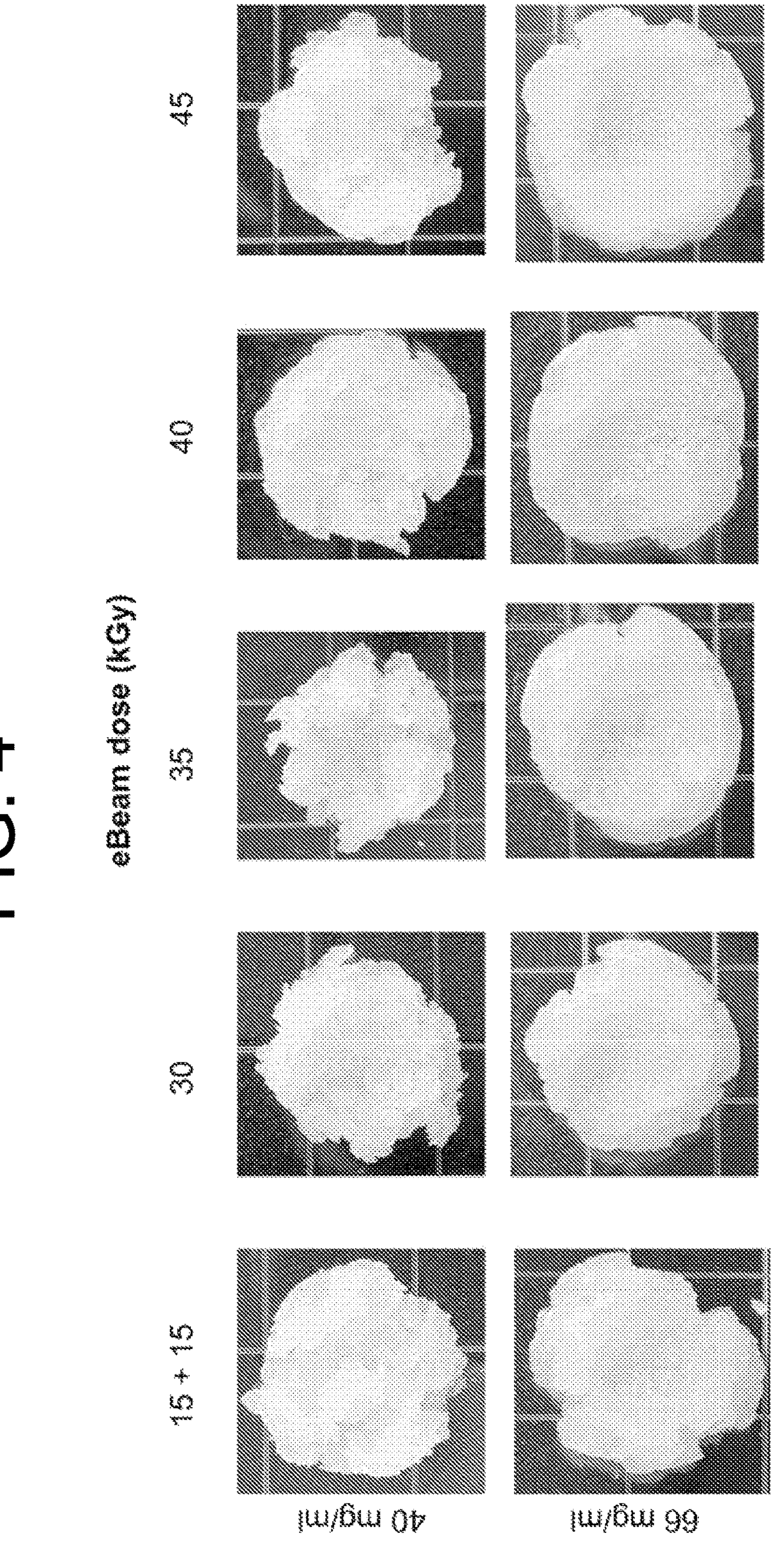
FIG. 4: Macroscopic Gelation tests at 37° C. with gentle manipulation. 5% colloid hydrogels containing 40 or 66 mg/ml trehalose were subjected to E-beam sterilization at the indicated dosages. After sterilization, the samples were chilled to 4° C. and injected into ring molds. The samples were then placed in a 37° C. incubator for 1 hr. After 1 hour the gels were manipulated by pressing down on the center. Macroscopic evaluation showed that dECM colloid hydrogels containing 40 mg/ml trehalose broke apart more easily under gentle manipulation than the colloid hydrogels containing 66 mg/ml trehalose.

Results showed that samples containing 66 mg/ml trehalose were able to hold their shape better than samples that were prepared with 40 mg/ml trehalose at all E-beam doses tested. Furthermore, gentle manipulation of the samples (by pressing down on the center the gel) showed that dECM colloid hydrogels containing 40 mg/ml trehalose broke apart more easily under gentle manipulation than the colloid hydrogels containing 66 mg/ml trehalose (FIG. 4).

Figure 5B:
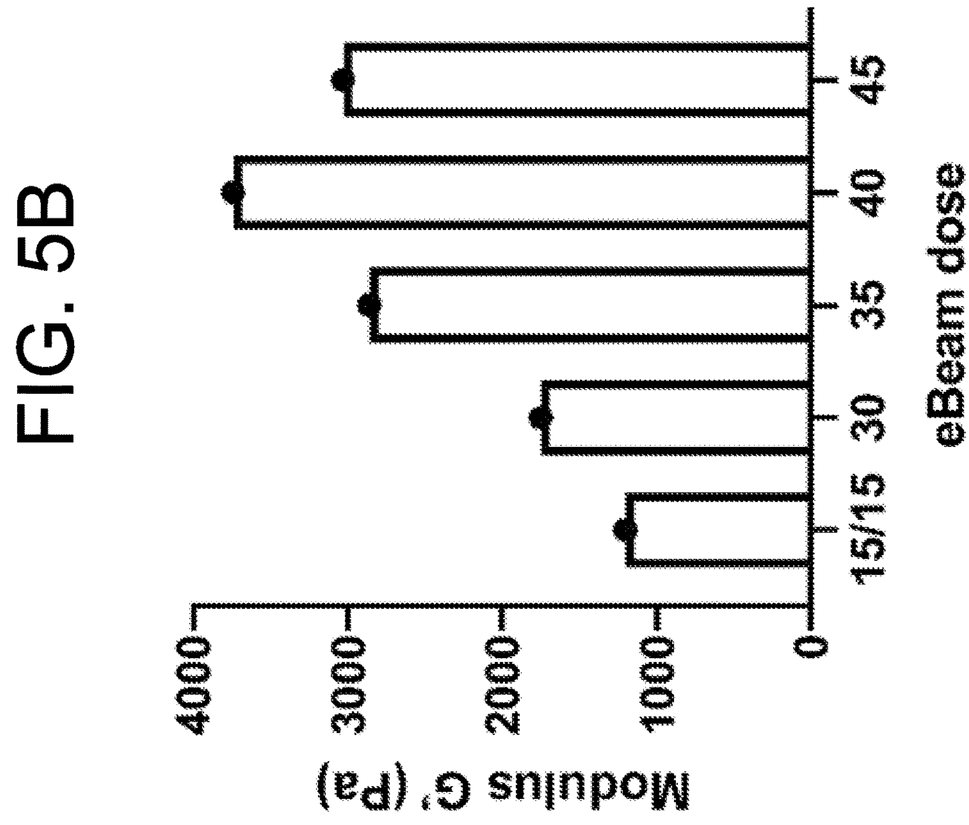
FIGS. 5A-5B: Viscoelastic characterization of dermal ECM colloid hydrogels containing Trehalose. (A) 2, 5, or 10% colloidal hydrogels containing 20 or 40 mg/ml trehalose were subjected to E-beam sterilization using a 25 kGy dose. The graph shows the average storage modulus of the samples. The results show that samples containing 20 mg/ml trehalose were more stiff than the 40 mg/ml samples; and increasing colloid concentrations increases the stiffness of the material. (B) Average storage modulus of a 5% colloidal hydrogel containing 66 mg/ml trehalose and sterilized by E-beam at 5 different doses.
Figure 5A:
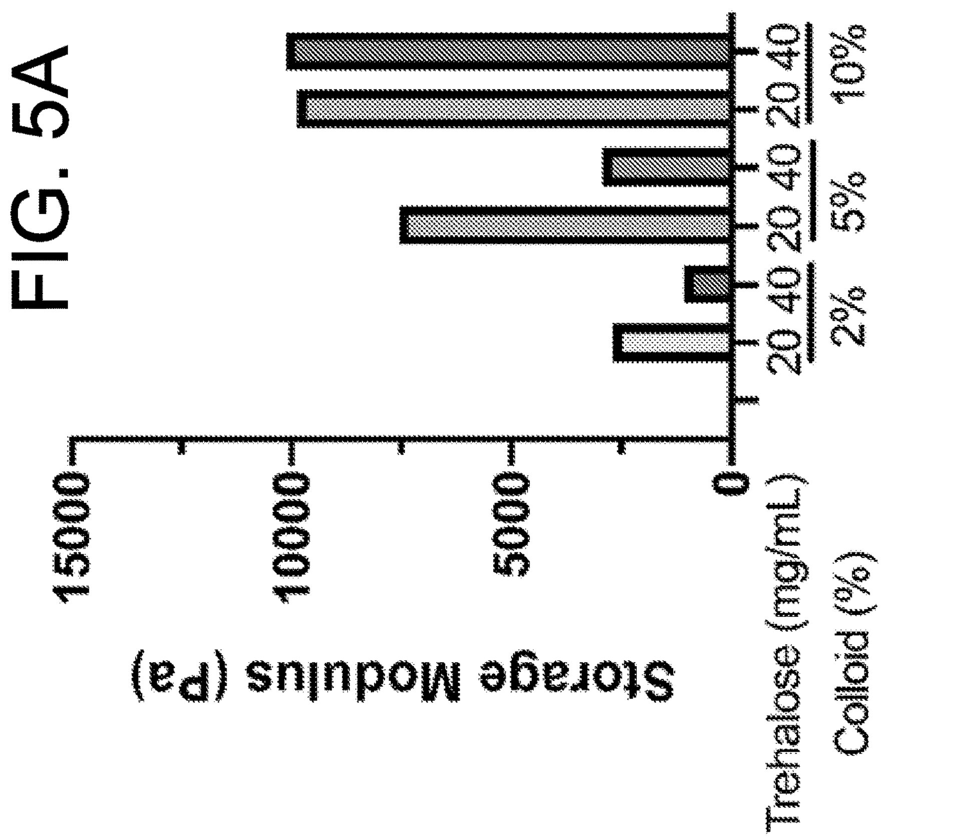

Next, the viscoelastic properties of dermal ECM colloid hydrogel containing Trehalose (FIGS. 5A-5B) were determined. 2, 5, or 10% colloidal hydrogels (w/v) containing 20 or 40 mg/ml trehalose were subjected to E-beam sterilization using a 25 kGy dose. The average storage modulus of the samples is shown in FIG. 5A. The results show that samples containing 20 mg/ml trehalose were more stiff than the 40 mg/ml samples; and increasing colloid concentrations increased the stiffness of the material.

Figure 6:
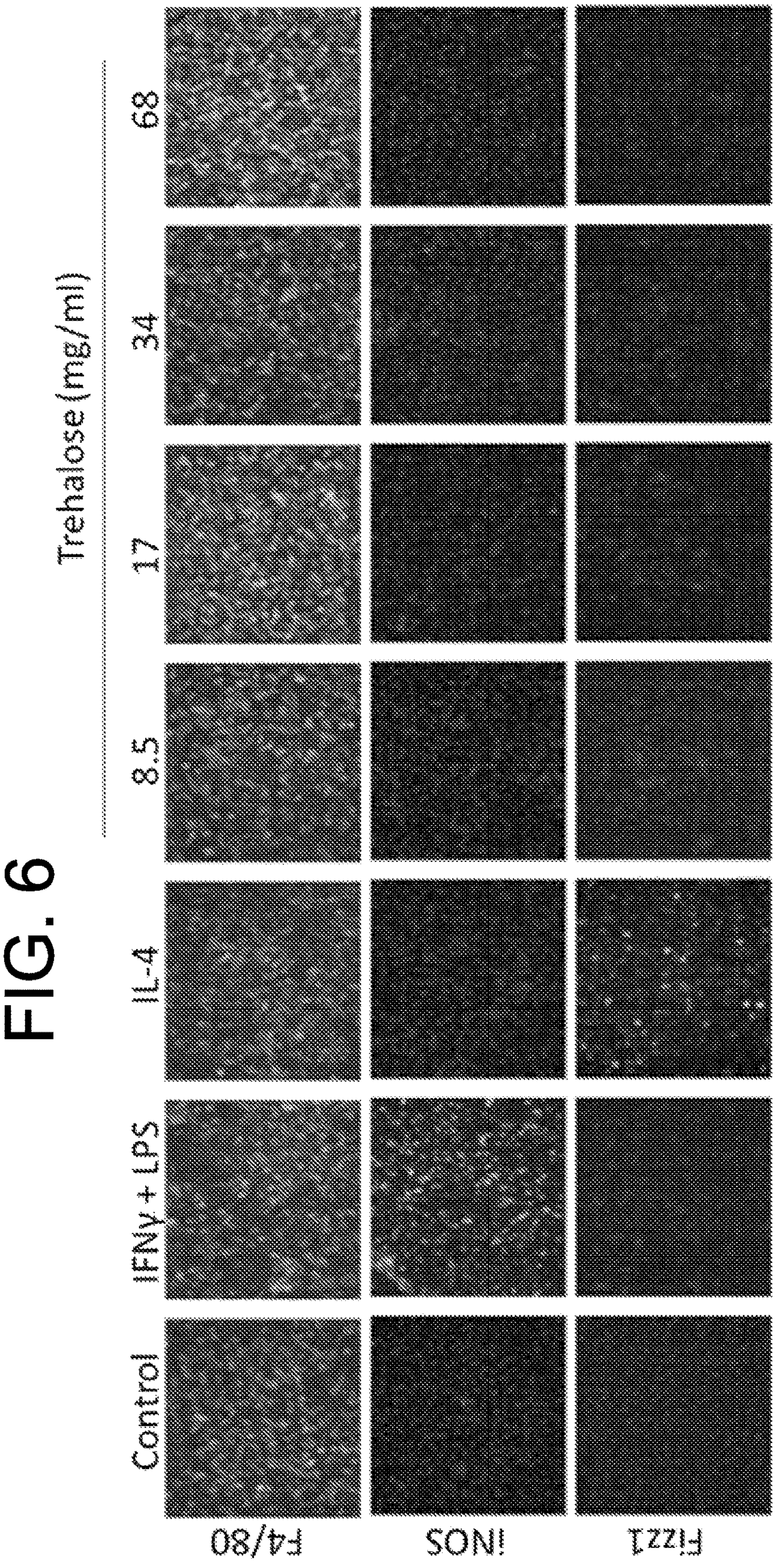
FIG. 6: Trehalose does not induce expression of iNOS or Resistin like beta ("RETNLB" or "Fizz1") in macrophages. Mouse bone marrow-derived macrophages were untreated (control) or treated with increasing concentrations of trehalose (8.5 to 68 mg/ml) for 24 hrs, fixed, and immunolabeled for strong indicators of the pro-inflammatory M1-like macrophage marker (iNos) or pro-remodeling M2-like macrophage marker (Fizz1), and counterstained with DAPI. Treatment of cells with IFNγ and lipopolysaccharide (LPS) was used as a positive control for the M1-like phenotype, and IL-4 was used as a positive control for the M2-like phenotype. F4/80 staining was used as a positive control for macrophages. Cells were imaged at 200×.

Finally, the bioactivity of trehalose toward murine bone marrow-derived macrophages was evaluated (FIG. 6). Results from the assay showed that compared to controls, trehalose was unable to induce expression of iNOS or Fizz1. In summary, the data show that trehalose can be used as an excipient in the preparation of acoustic gels and colloidal acoustic gels owing to its inert biological activity, and its ability to reduce the stiffness and prevent formation of aggregates in colloidal acoustic ECM hydrogels after E-beam sterilization, leading to a uniform consistency of the hydrogel.

Example 2

Materials and Methods

Preparation of Dermal ECM: Dermal ECM was prepared as previously described (Reing J E, et al. *Biomaterials.* 2010; 31(33):8626-33). Briefly, full-thickness skin was harvested from market-weight (~110 kg) pigs (Tissue Source Inc.), and the subcutaneous fat and epidermis were removed by mechanical delamination. This tissue was then treated with 0.25% trypsin (Thermo Fisher Scientific) for 6 hours, 70% ethanol for 10 hours, 3% $H_2O_2$ for 15 min, 1% Triton X-100 (Sigma-Aldrich) in 0.26% EDTA/0.69% tris for 6 hours with a solution change for an additional 16 hours, and 0.1% peracetic acid/4% ethanol (Rochester Midland) for 2 hours. Water washes were performed between each chemical change with alternating water and phosphate-buffered saline (PBS) washes following the final step. All chemical exposures were conducted under agitation on an orbital shaker at 300 rpm. Dermal ECM was then lyophilized and milled into particulate using a Wiley Mill with a #60 mesh screen.

Preparation of colloidal ECM hydrogels: 100 mg of ECM powder was resuspended in phosphate buffered saline (PBS) in a 50 mL conical tube with or without trehalose and sonicated with a FISHERBRAND™ Model 120 Sonic Dismembrator equipped with a ⅛" probe for 5 minutes at 100% amplitude. After sonication, the solubilized ECM solution was mixed with additional ECM powder to create 2, 5, or 10% (w/v) colloidal gel suspensions. After mixing the suspension, the samples were placed into 3 ml syringes and incubated at 4° C. to induce gelation.

Macrophage activation: Murine, bone marrow was harvested from 6- to 8-week-old B6 mice. Harvested cells from the bone marrow were washed and plated at $2\times10^6$ cells/mL and were allowed to differentiate into macrophages for 7 days in the presence of macrophage colony-stimulating factor (MCSF) with complete medium changes every 48 h. Macrophages were then activated for 24 h with one of the following: 1) 20 ng/mL Interferon-γ (IFNγ) and 100 ng/mL lipopolysaccharide (LPS) (Affymetrix eBioscience, Santa Clara, CA; Sigma Aldrich) to promote an $M_{IFN\gamma+LPS}$ phenotype (M1-like); 2) 20 ng/mL interleukin (IL)-4 (Invitrogen) to promote an $M_{IL-4}$ phenotype (M2-like); 3) increasing concentrations of trehalose (25, 50, 100, 200 mM) or 4) 5 mg/ml UBM acoustic gel. After a 24 hr incubation period at 37° C., cells were washed with sterile PBS and cells fixed with 2% paraformaldehyde (PFA) for immunolabeling. To prevent nonspecific binding, the cells were incubated in a blocking solution composed of PBS, 0.1% Triton-X, 0.1% Tween-20, 4% goat serum, and 2% bovine serum albumin for 1 h at room temperature. The blocking buffer was then removed and cells were incubated in primary antibodies. The cells were incubated at 4° C. for 16 h, the primary antibody was removed, and the cells washed with PBS. A solution of fluorophore-conjugated secondary antibody was added to the wells for 1 h at room temperature. The antibody was then removed, the cells washed with PBS, and the nuclei were counterstained using DAPI. Cytokine-activated macrophages were used to establish standardized exposure times (positive control), which were held constant throughout groups thereafter.

Example 3

Anal Fistula Repair

Current standard of care treatments for anal, rectal, and enterocutaneous fistulas remain ineffective and are associated with high complication rates presenting a persistent clinical challenge. Surgical approaches to treatment of fistula such as advancement flaps are associated with high fecal incontinence rates and poor outcomes. Alternatively, sphincter-preserving methods such as fistula plugs are associated with widely variable clinical outcomes due to plug extrusion, the main failure mechanism, and are often incompatible with complex fistula architectures which therefore require multiple interventions and long term draining seton placement. There are currently no treatment options available that preserve sphincter musculature, reduce complication and failure rates, are compatible with complex fistula, and promote timely healing of the fistula tract. An extracellular matrix (ECM) based, sheer-thinning hydrogel formulation may be a better solution for this unmet clinical need. ECM hydrogels and colloidal ECM hydrogels, prepared using the ultrasonic cavitation method, can be used to fill intersphincteric, transsphincteric, suprasphincteric, extrasphincteric or submucosal fistula tracts; and to reinforce and promote tract closure by allowing for timely host tissue integration without fecal incontinence or extrusion even in the case of complex and multi-tract fistulas. The ECM hydrogel can be injected into the fistula tract following debridement of the tract, with draining setons used preoperatively. Rheologic analysis showed that ECM hydrogels and colloidal ECM hydrogels can be easily administrated via catheter to effectively and timely repair fistulas by remaining in situ and allowing for host tissue integration and ultimately tract closure. The ECM hydrogel is intended to degrade within 7-120 days; and be replaced by new host tissue.

Figure 7C:
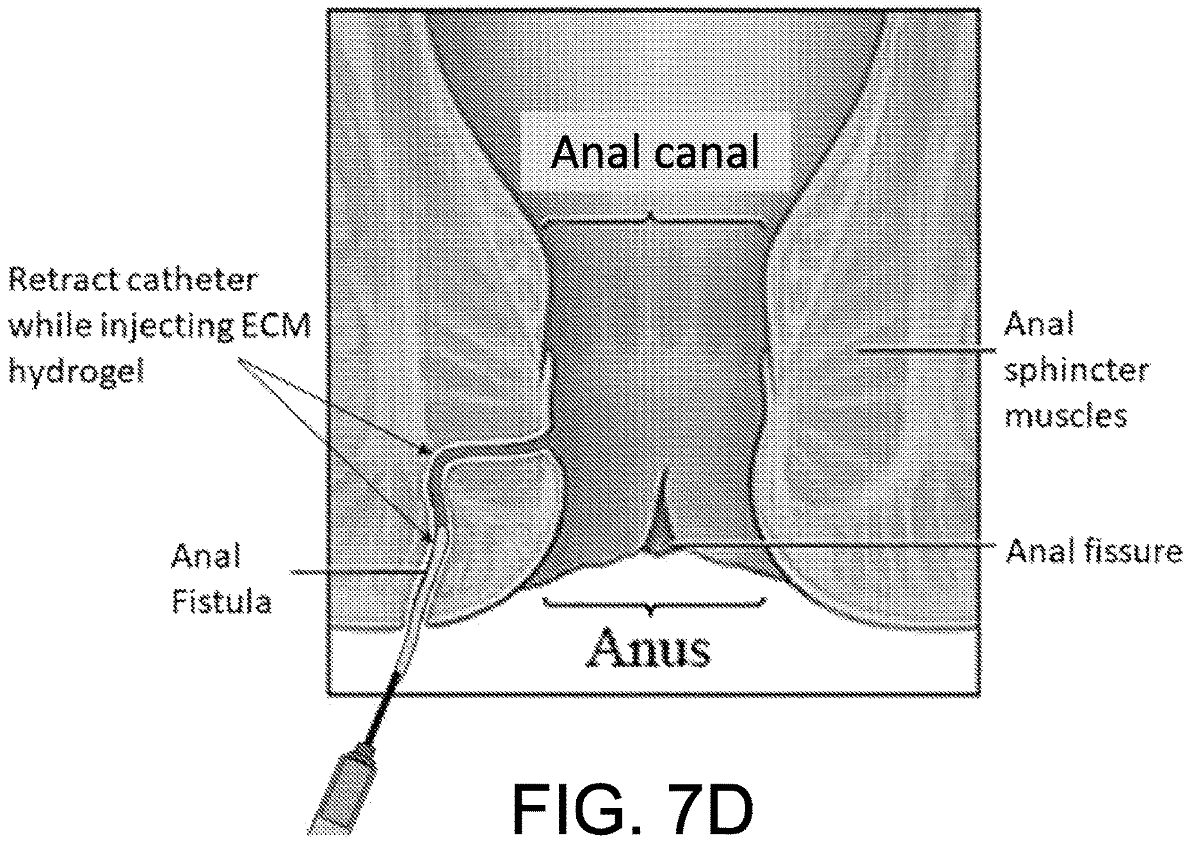
Figure 7D:
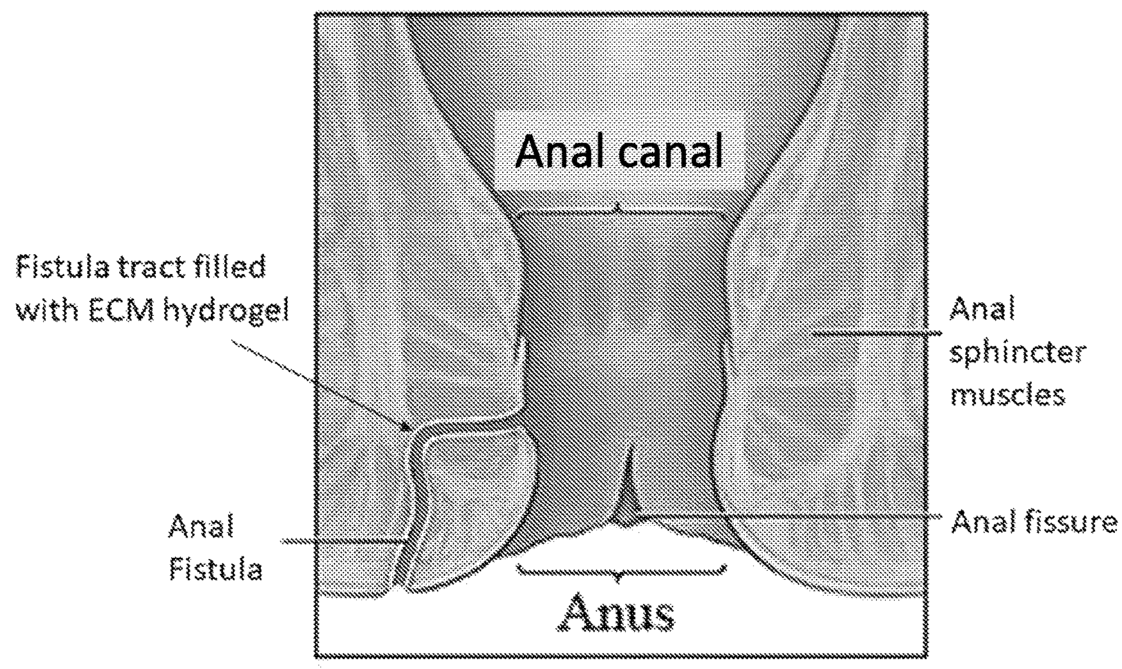
Figure 7D:
Figure 7E:

As shown in FIGS. 7A-D, a catheter may be used to introduce a sterilized acoustic ECM hydrogel into the tract of an anal fistula. In this case, the catheter is introduced through the external opening on the anal side of the fistula. The catheter is inserted through the fistula to the internal opening and the catheter is retracted to deposit the acoustic ECM hydrogel composition in the tract. Once the tract is filled, the catheter is removed. The acoustic ECM hydrogel remains as a gel in the tract at body temperature and does not leak out of the tract. This is shown in FIG. 7E which is a photograph of a pig with an anorectal fistula filled with the acoustic ECM hydrogel which is shown as the dark circle at approximately 11 o'clock of the anus. Further, because of its physical properties at body temperature, it retains sufficient stiffness to withstand the forces placed on the anorectal area during sitting and bowel movements.

For each surgery, a pig was placed on N.P.O. 12 hours pre-op to clear bowel contents. The pig was sedated with intramuscular injection of ketamine/xylazine (20 mg/kg (K) and 2 mg/kg (XY)) and telazol. Anesthesia was maintained throughout surgery with continuous isofluorane. The pig was positioned supine in dorsal lithotomy position. Incisions were made using an 11 blade scalpel into the ischioanal fossa as the 2-, 5-, 8-, and 11-o'clock position for a total of four fistulas. Using a curved hemostat, blunt dissection was performed through the anal sphincter musculature to the dentate line of the anal mucosa. A 1 mm incision was made at the dentate line to connect the tract. 14-french silicone draining setons were passed through the fistula, tied, and sutured to the skin to prevent movement. Setons were kept in place for 4 weeks post-operatively to establish patent tracts.

After 4 weeks, animals were sedated, placed in dorsal lithotomy position, and the setons were removed and the tracts cleaned with sequential washes of 70% EtOH and iodine scrub. Tracts were filled with dECM colloid gels and the internal opening of the fistula tracts were closed with a single 4-O figure-of-eight suture. The external openings remained open and were visualized for gel drainage.

In the case of repair of a fistula tract, it may also be possible to close one end of the tract with one or more sutures prior to instilling the ECM acoustic hydrogel. For example, if there is an opening at one that is large than the catheter, a suture can be placed to create a pocket to be filled with the hydrogel, for example, on the end that will be filled first. Further, one or more sutures can be placed on each end of the fistula to close the tissue around the hydrogel. This may be suitable in situations where the fistula is wide and not very long.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of treating a fistula in a subject, comprising:

administering locally to the fistula in the subject an effective amount of a composition comprising a mammalian extracellular matrix (ECM) hydrogel, wherein:

a) the mammalian ECM hydrogel is thermoreversible, wherein the mammalian ECM hydrogel is in a gel phase at temperatures below about 37° C. and transitions to a liquid phase at temperatures above about 37° C., b) the mammalian ECM hydrogel comprises solubilized ECM at a concentration of about 0.1 mg/mL to about 1,000 mg/mL, and c) the composition has a storage modulus (G') to loss modulus (G") ratio in the range of about 6:1 to about 12:1 at 37° C., thereby treating the fistula in the subject.

2. The method of claim 1, wherein the composition further comprises a radioprotectant, wherein the radioprotectant comprises 0.1 mg/mL to about 700 mg/mL trehalose.

3. The method of claim 2, further comprising sterilizing the composition with ionizing radiation.

4. The method of claim 3, wherein the ionizing radiation is e-beam or gamma irradiation.

5. The method of claim 1, wherein the mammalian ECM hydrogel comprises urinary bladder ECM, small intestinal submucosal (SIS) ECM, esophageal ECM, tracheal ECM, liver ECM, or dermal ECM.

6. The method of claim 1, wherein the mammalian ECM hydrogel comprises porcine ECM.

7. The method of claim 1, wherein the mammalian ECM hydrogel does not comprise an exogenous protease or an inactivated exogenous protease.

8. The method of claim 1, wherein the subject is a human.

9. The method of claim 2, wherein the composition comprises about 50 to about 500 mg/ml trehalose.

10. The method of claim 1, wherein the composition further comprises about 1% to about 30% weight per volume comminuted ECM that is not solubilized in the hydrogel.

11. The method of claim 1, wherein the composition has a storage modulus (G') of about 5 Pa to about 15,000 Pa.

12. The method claim 1, wherein the fistula is an anal fistula, and wherein the anal fistula is an intersphincteric, transsphincteric, suprasphincteric, extrasphincteric, or submucosal anal fistula.

13. The method of claim 1, wherein the composition is administered to fill a tract of the fistula.

14. A composition comprising:

i) a mammalian extracellular matrix (ECM) hydrogel, wherein:

a) the mammalian ECM hydrogel is thermoreversible, wherein the mammalian ECM hydrogel is in a gel phase at temperatures below about 37° C. and transitions to a liquid phase at temperatures above about 37° C., b) the mammalian ECM hydrogel comprises solubilized ECM at a concentration of about 0.1 mg/mL to about 1,000 mg/mL, and c) the composition has a storage modulus (G') to loss modulus (G") ratio of about 6:1 to about 12:1 at 37° C.;

ii) 0.1 mg/mL to about 700 mg/mL trehalose; and iii) about 1% to about 30% weight per volume of comminuted ECM that is not solubilized in the hydrogel.

15. The composition of claim 14, wherein the composition has been gamma irradiated.

16. The composition of claim 14, wherein the mammalian ECM hydrogel comprises urinary bladder ECM, small intestinal submucosal (SIS) ECM, esophageal ECM, trachea ECM, liver ECM, or dermal ECM.

17. The composition of claim 14, wherein the ECM comprises porcine ECM.

18. The composition of claim 14, wherein the mammalian ECM hydrogel does not comprise an exogenous protease or an inactivated exogenous protease.

19. The composition of claim 14, wherein the composition comprises about 50 mg/mL to about 500 mg/mL trehalose.

20. The composition claim 14, wherein the composition has a storage modulus (G') of about 5 Pa to about 15,000 Pa.

21. The method of claim 1, wherein the fistula is an enterocutaneous fistula, colocutaneous fistula, enteroenteral fistula, vesiconintestinal fistula, vesicocoli fistula, vesicorectal fistula, rectovaginal fistula, vesicovaginal fistula, rectouterine fistula, vesicouterine fistula, uretovaginal fistula, metroperitoneal fistula, enterovaginal fistula, tracheaesophageal fistula, anal fistula, anorectal fistula, biliary-enteric fistula, vesico-intestinal fistula, pancreatic fistula, cryptoglandular fistula, Crohn's fistula, dural-sinus fistula, colo-vesical fistula, colo-enteric fistula, colo-vaginal fistula, recto-urethral fistula, or pharyngo-cutaneous fistula.

* * * * *